US012297269B2

(12) United States Patent
Britanova et al.

(10) Patent No.: US 12,297,269 B2
(45) Date of Patent: May 13, 2025

(54) MONOCLONAL ANTIBODIES THAT BIND SPECIFICALLY TO HUMAN TRBV9

(71) Applicant: JOINT STOCK COMPANY "BIOCAD", Saint Petersburg (RU)

(72) Inventors: Olga Vladimirovna Britanova, Moscow (RU); Dmitry Borisovich Staroverov, Moscow (RU); Anna Valentinovna Evstrateva, G. Pitkyaranta (RU); Alexey Konstantinovich Misorin, Saint Petersburg (RU); Timofey Aleksandrovich Nemankin, Saint Petersburg (RU); Mariia Aleksandrovna Shchemeleva, Saint-Petersburg (RU); Anna Konstantinovna Vladimirova, Saint Petersburg (RU); Arina Vitalevna Anikina, Moscow (RU); Roman Alekseevich Ivanov, Moscow (RU); Dmitry Valentinovich Morozov, Saint Petersburg (RU); Pavel Andreevich Iakovlev, Saint Petersburg (RU); Sergey Anatolievich Lukyanov, Moscow (RU)

(*) Notice: Subject to any disclaimer, the term of this patent is extended or adjusted under 35 U.S.C. 154(b) by 993 days.

(21) Appl. No.: 17/417,570

(22) PCT Filed: Dec. 24, 2019

(86) PCT No.: PCT/RU2019/050257
§ 371 (c)(1),
(2) Date: Jun. 23, 2021

(87) PCT Pub. No.: WO2020/139171
PCT Pub. Date: Jul. 2, 2020

(65) Prior Publication Data
US 2022/0056133 A1    Feb. 24, 2022

(30) Foreign Application Priority Data

Dec. 25, 2018 (RU) .......................... RU2018146029

(51) Int. Cl.
C07K 16/28 (2006.01)
A61K 39/00 (2006.01)
(Continued)

(52) U.S. Cl.
CPC ...... *C07K 16/2809* (2013.01); *A61K 39/3955* (2013.01); *A61K 45/06* (2013.01);
(Continued)

(58) Field of Classification Search
CPC ............ C07K 16/2809; C07K 16/2803; A61K 2039/505; A61K 39/39558; A61P 37/00
See application file for complete search history.

(56) References Cited

U.S. PATENT DOCUMENTS 8,722,049 B2    5/2014   Getts et al.
2003/0039649 A1  2/2003   Foote
(Continued)

FOREIGN PATENT DOCUMENTS

CA    3042890 A1    5/2018
RU    2539032 C2    1/2015
(Continued)

OTHER PUBLICATIONS

Yunqian Zhao et al, "Autoimmune susceptibility imposed by public TCRB chains", Scientific Reports, 2016, 6:37543 (Year: 2016).*
(Continued)

*Primary Examiner* — Julie Wu
*Assistant Examiner* — Sonia Jessica Laurie
(74) *Attorney, Agent, or Firm* — Anglehart et al.

(57) ABSTRACT

A monoclonal humanized antibody or antigen-binding fragment thereof that specifically bind to the TRBV9 family of
(Continued)

the human T cell receptor. A nucleic acid encoding the antibody or antigen-binding fragment thereof, an expression vector, a method for preparing the antibody, and use of the antibody in treatment of diseases or disorders associated with the human T cell receptor family. The generation of antibodies that can be used for treating, in particular AS, celiac disease and malignant blood diseases, the pathogenesis of which involves the TRBV9 family TCRs.

22 Claims, 3 Drawing Sheets

Specification includes a Sequence Listing.

(51) Int. Cl.
A61K 39/395 (2006.01)
A61K 45/06 (2006.01)
(52) U.S. Cl.
CPC .... A61K 2039/505 (2013.01); C07K 2317/24 (2013.01); C07K 2317/92 (2013.01)

(56) References Cited

U.S. PATENT DOCUMENTS

| | | |
|---|---|---|
| 2010/0330571 A1 | 12/2010 | Robins et al. |
| 2020/0332003 A1 | 10/2020 | Britanova et al. |

FOREIGN PATENT DOCUMENTS

| | | | |
|---|---|---|---|
| RU | 2017145662 A | | 6/2019 |
| WO | 90/06758 A1 | | 6/1990 |
| WO | WO/1990/006758 | * | 6/1990 |
| WO | 94/05801 A1 | | 3/1994 |
| WO | WO/1994/005801 | * | 3/1994 |
| WO | 2012/008397 A1 | | 1/2012 |
| WO | 2014/177771 A1 | | 11/2014 |
| WO | 2017/137453 A1 | | 8/2017 |
| WO | 2017/216324 A1 | | 12/2017 |
| WO | 2018/155692 A1 | | 8/2018 |
| WO | 2019/132738 A1 | | 7/2019 |

OTHER PUBLICATIONS

Laura Kivela et al, "Current and emerging therapies for coeliac disease", Nat Rev Gastro Hepatol, 2020, 18:181-195 (Year: 2020).*
Jocelyn A. Silverster et al, "Celiac Disease: Fallacies and Facts", Am J Gastroenterol, 2021, 116:1148-1155 (Year: 2021).*
Carlo Cattasi et al, "Coeliac disease", Lancet, 2022, 99:2413-2426 (Year: 2022).*
Pauline Boulos et al, "Pharmacological Treatment of Ankylosing Spondylitis: A Systematic Review", Drugs, 2005, 65 (15): 2111-2127 (Year: 2005).*
Walter P. Maksymowych, "Update on the treatment of ankylosing spondylitis", Therapeutics and Clinical Risk Management, 2007, 3:6, 1125-1133, (Year: 2007).*
Marina Amaral de Avila Machado et al, "Treatment of ankylosing spondylitis with TNF blockers: a meta-analysis", Rhematology International, 2013, 33:2199-2213 (Year: 2013).*
Yufeng Yin et al, "Efficacy and safety of IL-17 inhibitors for the treatment of ankylosing spondylitis: a systematic review and meta-analysis", Arthritis Research & Therapy, 2020, 22:111 (Year: 2020).*
Elizabeth A. Raetz & David T. Teachey, "T-cell acute lymphoblastic leukemia", Hematol Am Soc Program 580-588, 2016 (Year: 2016).*
Mark R. Litznow and Adolofo A. Ferrando, "How I treat T-cell acute lymphoblastic leukemia in adults", Blood, 2015, vol. 126, No. 7, 833-841 (Year: 2015).*
Linda Hammerich et al, "Systemic clinical tumor regressions and potentiation of PD1 blockade with in situ vaccination", Nature Medicine, 2019, 25:814-824 (Year: 2019).*

Guido Ghilardi et al, "T cell lymphoma and secondary primary malignancy risk after commercial CAR T cell therapy", Nature Medicine, 2024, 30:984-989 (Year: 2024).*
Fanlin Li et al, "T cell receptor β-chain-targeting chimeric antigen receptor T cells against T cell malignancies", Nature Communications, 2022, 13:4334 (Year: 2022).*
Olivia M. Lucero et al, "Patient-Specific Targeting of the T-Cell Receptor Variable Region as a Therapeutic Strategy in Clonal T-Cell Diseases", Clinical Cancer Research, 2023 (Year: 2023).*
Olga V. Britanova et al, "Targeted depletion of TRBV9+ T cells as immunotherapy in a patient with ankylosing spondylitis", Nature Medicine, 2023, 29:2731-2736 (Year: 2023).*
Ekaterina A. Komech et al, "CD8+ T cells with characteristic T cell receptor beta motif are detected in blood and expanded in synovial fluid of ankylosing spondylitis patients", Rheumatology, 2018, 57:1097-1104 (Year: 2018).*
Xinbo Yang et al, "Autoimmunity-associated T cell receptors recognize HLA-B*27-bound peptides", Nature, 2022, 612:771-777 (Year: 2022).*
Jan Petersen et al, "Determinants of Gliadin-Specific T Cell Selection in Celiac Disease", J Immunol, 2015, 194 (12):6112-6122. (Year: 2015).*
S. Toyabe et al, "Biclonal expansion of T cells infected with monoclonal Epstein-Barr virus (EBV) in a patient with chronic, active EBV infection", Clin Exp Limmunol, 2003, 134:92-97 (Year: 2003).*
S. Toyabe, W. Harada & M. Uchiyama, "Biclonal expansion of T cells infected with monoclonal Epstein-Barr virus (EBV) in a patient with chronic, active EBV infection", Clin Exp Immunol 2003; 134:92-97, doi:10.1046/j.1365-2249.2003.02270.x (Year: 2003).*
Corresponding Japanese application No. 2021-537704 Office Action dated Oct. 17, 2023 (translation provided).
Corresponding Chinese application No. 201980092914.6 Office Action dated Sep. 21, 2023 (translation provided).
European application No. 19904442.1 the extended European search reportdated Aug. 10, 2022.
Israelson MA et al, "Testing of monoclonal antibodies against the T-cell receptor associated with ankylosing spondylitis", Preventive Medicine, (Dec. 1, 2018), No. (5)2018, doi:10.24075/brsmu.2018.064, ISSN 2500-1094, pp. 71-79, XP055820667 [I].
Marco De Simone et al, "Single Cell T Cell Receptor Sequencing: Techniques and Future Challenges", Frontiers in Immunology, (Jul. 18, 2018), vol. 9, doi:10.3389/fimmu.2018.01638, XP055698378.
Sophie E. Broughton et al, "Biased T Cell Receptor Usage Directed against Human Leukocyte Antigen DQ8-Restricted Gliadin Peptides Is Associated with Celiac Disease", Immunity, Amsterdam, NL, (Oct. 1, 2012), vol. 37, No. 4, doi:10.1016/j.immuni.2012.07.013, ISSN 1074-7613, pp. 611-621, XP055343915 [I].
Stephan Duebel ED—Stefan Dubel, Handbook of Therapeutic Antibodies Chapter 6, Handbook of Therapeutic Antibodies, Wiley-VCH, Weinheim, pp. 119-144, (Jan. 1, 2007), ISBN 978-3-527-31453-9, XP007913671.
Related International application No. PCT/RU2019/050257 International Search Report dated Apr. 30, 2020.
Related International application No. PCT/RU2019/050257 Translation of the ISR dated Apr. 30, 2020.
Related International application No. PCT/RU2019/050257 Written Opinion of the International Searching Authority dated Apr. 30, 2020.
Related International application No. PCT/RU2019/050257 English Translation of the Written Opinion of the International Searching Authority dated Apr. 30, 2020.
Toyabe S. et. al. Biclonal expansion of T cells infected with monoclonal Epstein-Barr virus (EBV) in a patient with chronic, active EBV infection. Clinical & Experimental Immunology, vol. 135, Is. 1, Oct. 2003, pp. 92-97, Sep. 8, 2003.
Zhijun Liu et al., Prevention of Type 1 Diabetes in the Rat With an Allele-Specific Anti-T-Cell Receptor Antibody. Diabetes, vol. 61, No. 5, May 19, 2012 (May 19, 2012), pp. 1160-1168.
Faham Malek et al., Discovery of T Cell Receptor β Motifs Specific to HLA-B27-Positive Ankylosing Spondylitis by Deep Repertoire Sequence Analysis. Arthritis & Rheumatology (Hoboken), vol. 69, No. 4, Mar. 29, 2017 (Mar. 29, 2017), pp. 774-784.

(56) References Cited

OTHER PUBLICATIONS

S. Toyabe et al., Biclonal expansion of T cells infected with monoclonal Epstein-Barr virus (EBV) in a patient with chronic, active EBV infection. Clinical and Experimental Immunology, vol. 134, No. 1, Oct. 1, 2003 (Oct. 1, 2003), pp. 92-97.

Konig M. et al., Tregalizumab—A Monoclonal Antibody to Target Regulatory T Cells. Front Immunol Jan. 25, 2016; 7:11. pp. 1-7.

Haroon N et al., The Impact of Tumor Necrosis Factor α Inhibitors on Radiographic Progression in Ankylosing Spondylitis. Arthritis Rheum. Oct. 2013;65(10):2645-2654.

Duarte J. et al., Modulation of IL-17 and Foxp3 Expression in the Prevention of Autoimmune Arthritis in Mice. PloS One May 10, 2010;5(5):e10558.

Marie-Paule Lefranc, IMGT, the international ImMunoGeneTics database. Nucleic Acids Research, vol. 29, Issue 1, Jan. 1, 2001, pp. 207-209.

Petersen J et al., Determinants of Gliadin-Specific T Cell Selection in Celiac Disease. J Immunol. 2015; 194(12):6112-6122.

Brennan et al., Heterogeneity of T cell receptor idiotypes in rheumatoid arthritis . . . Clin Exp Immunol. Sep. 1988; 73(3):417-423.

Taylor L.D. et al. A transgenic mouse that expresses a diversity of human sequence heavy and light chain immunoglobulins. Nucleic Acids Research, vol. 20, Issue 23, Dec. 11, 1992, pp. 6287-6295.

Huston et al. Protein engineering of antibody binding sites: recovery of specific activity in an anti-digoxin single-chain Fv analogue produced in *Escherichia coli*. (1988) Proc. Natl. Acad. Sci. USA 85:5879-5883.

Holliger P. et al. "Diabodies": small bivalent and bispecific antibody fragments. (1993) Proc. Natl. Acad. Sci. USA 90:6444-6448.

Poljak R.J. et al. Production and structure of diabodies. (1994) Structure 2:1121-1123.

Kipriyanov S.M. et al. Single-chain antibody streptavidin fusions: Tetrameric bifunctional scFv-complexes with biotin binding activity and enhanced affinity to antigen. (1995) Human Antibodies and Hybridomas 6:93-101.

Colicelli et al., A temperature-sensitive mutation constructed by "linker insertion" mutagenesis. Mol. Gen. Genet. (1985) 199:537-539.

Olga V. Britanova et al., Dynamics of Individual T Cell Repertoires: From Cord Blood to Centenarians. J Immunol, 2016, 196(12) 5005-5013.

Xu et al. High-level expression of recombinant IgG1 by Cho K1 platform. Frontiers of Chemical Science and Engineering vol. 9, pp. 376-380 (2015).

Pluckthun, Antibodies from *Escherichia coli*. The Pharmacology of Monoclonal Antibodies, vol. 113, Rosenburg and Moore eds., Springer-Verlag, New York, p. 269-315, 1994.

Turner SJ et al., Structural determinants of T-cell receptor bias in immunity. Nature Reviews Immunology 2006, V.6, 883-894.

Ward et al. Binding activities of a repertoire of single immunoglobulin variable domains secreted from *Escherichia coli*. Nature vol. 341, pp. 544-546 (1989).

Bird et al. Single-chain antigen-binding proteins. (1988) Science 242:423-426.

Kipriyanov S.M. et al. Recombinant single-chain Fv fragments carrying C-terminal cysteine residues: Production of bivalent and biotinylated miniantibodies. (1994) Mol. Immunol., 31:1047-1058.

Barany, Single-stranded hexameric linkers: a system for in-phase insertion mutagenesis and protein engineering. Gene (1985) 37: 111-123.

Corresponding European application No. 19904442.1 Examination report dated Apr. 26, 2024.

\* cited by examiner

SEQUENCE LISTING

```
<160> NUMBER OF SEQ ID NOS: 22

<210> SEQ ID NO 1
<211> LENGTH: 5
<212> TYPE: PRT
<213> ORGANISM: Artificial
<220> FEATURE:
<223> OTHER INFORMATION: The HCDR1 sequence of the parental antibody
      TRBV9-2

<400> SEQUENCE: 1

Asp Tyr Leu Val His
1               5

<210> SEQ ID NO 2
<211> LENGTH: 17
```

```
<212> TYPE: PRT
<213> ORGANISM: Artificial
<220> FEATURE:
<223> OTHER INFORMATION: The HCDR2 sequence of the parental antibody
      TRBV9-2

<400> SEQUENCE: 2

Trp Ile Asn Thr Tyr Thr Gly Thr Pro Thr Tyr Ala Asp Asp Phe Glu
1               5                   10                  15

Gly

<210> SEQ ID NO 3
<211> LENGTH: 13
<212> TYPE: PRT
<213> ORGANISM: Artificial
<220> FEATURE:
<223> OTHER INFORMATION: The HCDR3 sequence of the parental antibody
      TRBV9-2

<400> SEQUENCE: 3

Ser Trp Arg Arg Gly Leu Arg Gly Ile Gly Phe Asp Tyr
1               5                   10

<210> SEQ ID NO 4
<211> LENGTH: 11
<212> TYPE: PRT
<213> ORGANISM: Artificial
<220> FEATURE:
<223> OTHER INFORMATION: The LCDR1 sequence of the parental antibody
      TRBV9-2

<400> SEQUENCE: 4

Lys Ala Ser Lys Ser Ile Asn Lys Tyr Leu Ala
1               5                   10

<210> SEQ ID NO 5
<211> LENGTH: 7
<212> TYPE: PRT
<213> ORGANISM: Artificial
<220> FEATURE:
<223> OTHER INFORMATION: The LCDR2 sequence of the parental antibody
      TRBV9-2

<400> SEQUENCE: 5

Asp Gly Ser Thr Leu Gln Ser
1               5

<210> SEQ ID NO 6
<211> LENGTH: 9
<212> TYPE: PRT
<213> ORGANISM: Artificial
<220> FEATURE:
<223> OTHER INFORMATION: The LCDR3 sequence of the parental antibody
      TRBV9-2

<400> SEQUENCE: 6

Gln Gln His Asn Glu Tyr Pro Pro Thr
1               5

<210> SEQ ID NO 7
<211> LENGTH: 366
<212> TYPE: DNA
<213> ORGANISM: Artificial
<220> FEATURE:
<223> OTHER INFORMATION: The nucleotide sequence of the variable domain
      of the heavy chain of the parental antibody TRBV9-2

<400> SEQUENCE: 7
```

```
caaatacaac tggtgcagag cgggccagaa ttgagagaac ccggagaatc tgtgaagctg    60
agttgtaagg ccagcggata cactttcact gactatctcg tgcactgggt gaaacaggct   120
cccggtaagg gattgaaatg gatgggatgg atcaatactt ataccggcac acctacatat   180
gcagacgatt tcgaggggcg atttgtgttc agtttgagg cctctgccag cacggcgaac   240
ctgcagatat cgaatctcaa gaatgaggac accgccacgt atttctgcgc tagatcttgg   300
agacgcggat tgagaggtat cggattcgac tactggggac aaggcgtctt cgtgactgta   360
tcatcc                                                              366
```

<210> SEQ ID NO 8
<211> LENGTH: 122
<212> TYPE: PRT
<213> ORGANISM: Artificial
<220> FEATURE:
<223> OTHER INFORMATION: The amino acid sequence of the variable domain
      of the heavy chain of the parental antibody TRBV9-2

<400> SEQUENCE: 8

```
Gln Ile Gln Leu Val Gln Ser Gly Pro Glu Leu Arg Glu Pro Gly Glu
1               5                   10                  15

Ser Val Lys Leu Ser Cys Lys Ala Ser Gly Tyr Thr Phe Thr Asp Tyr
            20                  25                  30

Leu Val His Trp Val Lys Gln Ala Pro Gly Lys Gly Leu Lys Trp Met
        35                  40                  45

Gly Trp Ile Asn Thr Tyr Thr Gly Thr Pro Thr Tyr Ala Asp Asp Phe
    50                  55                  60

Glu Gly Arg Phe Val Phe Ser Leu Glu Ala Ser Ala Ser Thr Ala Asn
65                  70                  75                  80

Leu Gln Ile Ser Asn Leu Lys Asn Glu Asp Thr Ala Thr Tyr Phe Cys
                85                  90                  95

Ala Arg Ser Trp Arg Arg Gly Leu Arg Gly Ile Gly Phe Asp Tyr Trp
            100                 105                 110

Gly Gln Gly Val Phe Val Thr Val Ser Ser
        115                 120
```

<210> SEQ ID NO 9
<211> LENGTH: 321
<212> TYPE: DNA
<213> ORGANISM: Artificial
<220> FEATURE:
<223> OTHER INFORMATION: The nucleotide sequence of the light chain
      variable domain of the parental antibody TRBV9-2

<400> SEQUENCE: 9

```
gatgtacaga tgacacaatc accctacaac cttgctgctt cccctgggga aagtgtcagt    60
atcaattgca aggcatcgaa gtcgatcaac aagtatcttg cgtggtatca gcagaagcca   120
ggaaagccca acaagctcct gatctatgac ggctctacac tgcaatctgg catacctcg    180 cggttttctg gctcggggtc cgggactgac ttcactctta caatacgagg acttgaaccc   240
gaagacttcg gcctgtatta ctgccagcag cacaatgagt atccacctac cttcgggct   300 ggcaccaagt tggagcttaa g                                             321
```

<210> SEQ ID NO 10
<211> LENGTH: 107
<212> TYPE: PRT
<213> ORGANISM: Artificial
<220> FEATURE:

<223> OTHER INFORMATION: The amino acid sequence of the light chain
      variable domain of the parent antibody TRBV9-2

<400> SEQUENCE: 10

Asp Val Gln Met Thr Gln Ser Pro Tyr Asn Leu Ala Ala Ser Pro Gly
1               5                   10                  15

Glu Ser Val Ser Ile Asn Cys Lys Ala Ser Lys Ser Ile Asn Lys Tyr
            20                  25                  30

Leu Ala Trp Tyr Gln Gln Lys Pro Gly Lys Pro Asn Lys Leu Leu Ile
        35                  40                  45

Tyr Asp Gly Ser Thr Leu Gln Ser Gly Ile Pro Ser Arg Phe Ser Gly
    50                  55                  60

Ser Gly Ser Gly Thr Asp Phe Thr Leu Thr Ile Arg Gly Leu Glu Pro
65                  70                  75                  80

Glu Asp Phe Gly Leu Tyr Tyr Cys Gln Gln His Asn Glu Tyr Pro Pro
                85                  90                  95

Thr Phe Gly Ala Gly Thr Lys Leu Glu Leu Lys
            100                 105

<210> SEQ ID NO 11
<211> LENGTH: 639
<212> TYPE: DNA
<213> ORGANISM: Artificial
<220> FEATURE:
<223> OTHER INFORMATION: The nucleotide sequence of the light chain
      of the parental antibody TRBV9-2

<400> SEQUENCE: 11
gacgtgcaga tgacccagtc ccctacaac ctggccgcct ccccggcga gtccgtgtcc      60 atcaactgca aggcctccaa gtccatcaac aagtacctgg cctggtacca gcagaagccc    120
ggcaagccca acaagctgct gatctacgac ggctccaccc tgcagtccgg catcccctcc    180
aggttctccg gctccggctc cggcaccgac ttcaccctga ccatcagggg cctggagccc    240
gaggacttcg gcctgtacta ctgccagcag cacaacgagt accccccac cttcggcgcc     300 ggcaccaagc tggagctgaa gcgaactgtg gctgcaccat ctgtcttcat cttcccgcca    360
tctgatgagc agttgaaatc tggaactgcc tctgtcgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgtcctcgc ccgtcacaaa gagcttcaac aggggagag                          639

<210> SEQ ID NO 12
<211> LENGTH: 213
<212> TYPE: PRT
<213> ORGANISM: Artificial
<220> FEATURE:
<223> OTHER INFORMATION: The amino acid sequence of the light chain
      of the parental antibody TRBV9-2

<400> SEQUENCE: 12

Asp Val Gln Met Thr Gln Ser Pro Tyr Asn Leu Ala Ala Ser Pro Gly
1               5                   10                  15

Glu Ser Val Ser Ile Asn Cys Lys Ala Ser Lys Ser Ile Asn Lys Tyr
            20                  25                  30

Leu Ala Trp Tyr Gln Gln Lys Pro Gly Lys Pro Asn Lys Leu Leu Ile
        35                  40                  45

```
Tyr Asp Gly Ser Thr Leu Gln Ser Gly Ile Pro Ser Arg Phe Ser Gly
    50                  55                  60

Ser Gly Ser Gly Thr Asp Phe Thr Leu Thr Ile Arg Gly Leu Glu Pro
 65                  70                  75                  80

Glu Asp Phe Gly Leu Tyr Tyr Cys Gln Gln His Asn Glu Tyr Pro Pro
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu
        210

<210> SEQ ID NO 13
<211> LENGTH: 1365
<212> TYPE: DNA
<213> ORGANISM: Artificial
<220> FEATURE:
<223> OTHER INFORMATION: The nucleotide sequence of the heavy chain
      of the parental antibody TRBV9-2

<400> SEQUENCE: 13
cagatccagc tggtgcagtc cggccccgag ctgagggagc ccggcgagtc cgtgaagctg      60
tcctgcaagg cctccggcta caccttcacc gactacctgg tgcactgggt gaagcaggcc    120
cccggcaagg gcctgaagtg gatgggctgg atcaacacct acaccggcac ccccacctac    180
gccgacgact cgagggcag gttcgtgttc tccctggagg cctccgcctc caccgccaac    240
ctgcagatct ccaacctgaa gaacgaggac accgccacct acttctgcgc caggtcctgg    300
aggaggggcc tgaggggcat cggcttcgac tactggggcc agggcgtgtt cgtgaccgtg    360
tcctccgcct ccaccaaggg cccatcggtc ttccccctgg cacccagctc caagagcacc    420
tctgggggca gcgcggccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgactgtgc cctctagcag cttgggcacc    600
cagacctaca tctgcaacgt gaatcacaag cccagcaaca ccaaggtgga caagaaagtt    660
gagcccccga atcttgtga caaaactcac acatgcccac cgtgcccagc acctgaactc    720
ctggggggac cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
aatggcaagg agtacaagtg caaggtctcc aacaaagccc tcccagcccc catcgagaaa   1020
accatctcca agcaaaagg gcagcccga gaaccacagg tgtacaccct gcccccatcc   1080
```

```
cgggatgagc tgaccaagaa ccaggtcagc ctgacctgcc tggtcaaagg cttctatccc    1140
agcgacatcg ccgtggagtg ggagagcaat gggcagccgg agaacaacta caagaccacg    1200
cctcccgtgc tggactccga cggctccttc ttcctctaca gcaagctcac cgtggacaag    1260
agcaggtggc agcaggggaa cgtcttctca tgctccgtga tgcatgaggc tctgcacaac    1320
cactacacgc agaagagcct ctccctgtct ccgggtaaat gataa                    1365
```

<210> SEQ ID NO 14
<211> LENGTH: 453
<212> TYPE: PRT
<213> ORGANISM: Artificial
<220> FEATURE:
<223> OTHER INFORMATION: The amino acid sequence of heavy chain
      of the parental antibody TRBV9-2

<400> SEQUENCE: 14

```
Gln Ile Gln Leu Val Gln Ser Gly Pro Glu Leu Arg Glu Pro Gly Glu
1               5                   10                  15

Ser Val Lys Leu Ser Cys Lys Ala Ser Gly Tyr Thr Phe Thr Asp Tyr
            20                  25                  30

Leu Val His Trp Val Lys Gln Ala Pro Gly Lys Gly Leu Lys Trp Met
        35                  40                  45

Gly Trp Ile Asn Thr Tyr Thr Gly Thr Pro Thr Tyr Ala Asp Asp Phe
    50                  55                  60

Glu Gly Arg Phe Val Phe Ser Leu Glu Ala Ser Ala Ser Thr Ala Asn
65                  70                  75                  80

Leu Gln Ile Ser Asn Leu Lys Asn Glu Asp Thr Ala Thr Tyr Phe Cys
                85                  90                  95

Ala Arg Ser Trp Arg Arg Gly Leu Arg Gly Ile Gly Phe Asp Tyr Trp
            100                 105                 110

Gly Gln Gly Val Phe Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 15
<211> LENGTH: 366
<212> TYPE: DNA
<213> ORGANISM: Artificial
<220> FEATURE:
<223> OTHER INFORMATION: The nucleotide sequence of the variable heavy
      chain of the antibody MA-042

<400> SEQUENCE: 15
caggtgcaac ttgttcagtc ggggagcgaa cttaagaagc caggggaaag tgtaaaagtg     60
agctgcaaag cctcaggcta cacgtttacc gattatcttg tgcattgggt tagacaggct    120
ccaggtcaag gactggaatg gatgggatgg atcaatacct atacagggac acccacatat    180
gccgatgact ttgagggacg gtttgtcttc tcacttgata ccagtgtttc cactgctaac    240
ctccagataa gcagcctgaa ggcagaggac accgccgttt atttctgcgc cgatcatgg     300 aggagaggct gcgaggaat tggattcgat tactggggtc agggcacttt agtcactgtc    360
tctagc                                                              366

<210> SEQ ID NO 16
<211> LENGTH: 122
<212> TYPE: PRT
<213> ORGANISM: Artificial
<220> FEATURE:
<223> OTHER INFORMATION: The amino acid sequence of the variable domain
      of the heavy chain of the parental antibody MA-042

<400> SEQUENCE: 16

Gln Val Gln Leu Val Gln Ser Gly Ser Glu Leu Lys Lys Pro Gly Glu
1               5                   10                  15

Ser Val Lys Val Ser Cys Lys Ala Ser Gly Tyr Thr Phe Thr Asp Tyr
            20                  25                  30

Leu Val His Trp Val Arg Gln Ala Pro Gly Gln Gly Leu Glu Trp Met
        35                  40                  45

Gly Trp Ile Asn Thr Tyr Thr Gly Thr Pro Tyr Ala Asp Asp Phe
    50                  55                  60

Glu Gly Arg Phe Val Phe Ser Leu Asp Thr Ser Val Ser Thr Ala Asn

```
                65                  70                  75                  80
Leu Gln Ile Ser Ser Leu Lys Ala Glu Asp Thr Ala Val Tyr Phe Cys
                        85                  90                  95

Ala Arg Ser Trp Arg Arg Gly Leu Arg Gly Ile Gly Phe Asp Tyr Trp
                        100                 105                 110

Gly Gln Gly Thr Leu Val Thr Val Ser Ser
                        115                 120
```

<210> SEQ ID NO 17
<211> LENGTH: 321
<212> TYPE: DNA
<213> ORGANISM: Artificial
<220> FEATURE:
<223> OTHER INFORMATION: The nucleotide sequence of the variable light
      chain of the antibody MA-042

<400> SEQUENCE: 17

```
gacatacaga tgactcaaag cccttattcg ctcagtgcgt cggtcgggga cagagtaacc    60
atcacctgca aggcgtcaaa gtcaatcaat aagtatctgg cgtggttcca gcagaagcca   120
ggaaagccta acaagctatt aatatacgat gggtctaccc tccaatccgg ggtcccttca   180
cgattttctg gaagcggctc aggaaccgat ttcacgctga ccatcagtag cttggagcct   240
gaggactttg ccacttatta ttgccagcag cacaacgagt atcctcccac cttcggacag   300
ggtacaaaac tggagatcaa g                                             321
```

<210> SEQ ID NO 18
<211> LENGTH: 107
<212> TYPE: PRT
<213> ORGANISM: Artificial
<220> FEATURE:
<223> OTHER INFORMATION: The amino acid sequence of variable light chain
      of the antibody MA-042

<400> SEQUENCE: 18

```
Asp Ile Gln Met Thr Gln Ser Pro Tyr Ser Leu Ser Ala Ser Val Gly
1               5                   10                  15

Asp Arg Val Thr Ile Thr Cys Lys Ala Ser Lys Ser Ile Asn Lys Tyr
                20                  25                  30

Leu Ala Trp Phe Gln Gln Lys Pro Gly Lys Pro Asn Lys Leu Leu Ile
            35                  40                  45

Tyr Asp Gly Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln His Asn Glu Tyr Pro Pro
                85                  90                  95

Thr Phe Gly Gln Gly Thr Lys Leu Glu Ile Lys
                100                 105
```

<210> SEQ ID NO 19
<211> LENGTH: 1356
<212> TYPE: DNA
<213> ORGANISM: Artificial
<220> FEATURE:
<223> OTHER INFORMATION: The nucleotide sequence of the heavy chain of
      the antibody MA-042

<400> SEQUENCE: 19

```
caggtgcaac ttgttcagtc ggggagcgaa cttaagaagc caggggaaag tgtaaaagtg    60
```

-continued

```
agctgcaaag cctcaggcta cacgtttacc gattatcttg tgcattgggt tagacaggct    120
ccaggtcaag gactggaatg gatgggatgg atcaatacct atacagggac acccacatat    180
gccgatgact ttgagggacg gtttgtcttc tcacttgata ccagtgtttc cactgctaac    240
ctccagataa gcagcctgaa ggcagaggac accgccgttt atttctgcgc ccgatcatgg    300
aggagaggcc tacgaggaat cggattcgat tactggggtc agggcacttt agtcactgtc    360
tctagcgcta gcaccaaggg cccatcggtc ttccccctgg cacccctcct caagagcacc    420
tctgggggca gcgcgccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagagagtt    660
gagcccaaat cttgtgacaa aactcacaca tgcccaccgt gcccagcacc tgaactcctg    720
gggggaccgt cagtcttcct cttccccca aaacccaagg acaccctcat gatctcccgg    780
acccctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagccctcc cagcccccat cgagaaaacc   1020
atctccaaag ccaagggca gccccgagaa ccacaggtgt acaccctgcc cccatcccgg   1080
gaggagatga ccaagaacca ggtcagcctg acctgcctgg tcaaaggctt ctatcccagc   1140
gacatcgccg tggagtggga gagcaatggg cagccggaga acaactacaa gaccacgcct   1200
cccgtgctgg actccgacgg ctccttcttc ctctatagca agctcaccgt ggacaagagc   1260
aggtggcagc aggggaacgt cttctcatgc tccgtgatgc atgaggctct gcacaaccac   1320
tacacgcaga aaagcctctc cctgtccccg ggtaaa                             1356
```

<210> SEQ ID NO 20
<211> LENGTH: 452
<212> TYPE: PRT
<213> ORGANISM: Artificial
<220> FEATURE:
<223> OTHER INFORMATION: The amino acid sequence of the heavy chain of
      the antibody MA-042

<400> SEQUENCE: 20

```
Gln Val Gln Leu Val Gln Ser Gly Ser Glu Leu Lys Lys Pro Gly Glu
1               5                   10                  15

Ser Val Lys Val Ser Cys Lys Ala Ser Gly Tyr Thr Phe Thr Asp Tyr
            20                  25                  30

Leu Val His Trp Val Arg Gln Ala Pro Gly Gln Gly Leu Glu Trp Met
        35                  40                  45

Gly Trp Ile Asn Thr Tyr Thr Gly Thr Pro Thr Tyr Ala Asp Asp Phe
    50                  55                  60

Glu Gly Arg Phe Val Phe Ser Leu Asp Thr Ser Val Ser Thr Ala Asn
65                  70                  75                  80

Leu Gln Ile Ser Ser Leu Lys Ala Glu Asp Thr Ala Val Tyr Phe Cys
                85                  90                  95

Ala Arg Ser Trp Arg Arg Gly Leu Arg Gly Ile Gly Phe Asp Tyr Trp
            100                 105                 110

Gly Gln Gly Thr Leu Val Thr Val Ser Ser Ala Ser Thr Lys Gly Pro
        115                 120                 125
```

| | | | | | | | | | | | |
|---|---|---|---|---|---|---|---|---|---|---|---|
|Ser|Val|Phe|Pro|Leu|Ala|Pro|Ser|Ser|Lys|Ser|Thr|Ser|Gly|Gly|Thr|
| |130| | | |135| | | |140| | | | | | |
|Ala|Ala|Leu|Gly|Cys|Leu|Val|Lys|Asp|Tyr|Phe|Pro|Glu|Pro|Val|Thr|
|145| | | |150| | | |155| | | | | | |160|
|Val|Ser|Trp|Asn|Ser|Gly|Ala|Leu|Thr|Ser|Gly|Val|His|Thr|Phe|Pro|
| | | |165| | | |170| | | |175| | | | |
|Ala|Val|Leu|Gln|Ser|Ser|Gly|Leu|Tyr|Ser|Leu|Ser|Ser|Val|Val|Thr|
| | | |180| | | |185| | | |190| | | | |
|Val|Pro|Ser|Ser|Ser|Leu|Gly|Thr|Gln|Thr|Tyr|Ile|Cys|Asn|Val|Asn|
| | | |195| | | |200| | | |205| | | | |
|His|Lys|Pro|Ser|Asn|Thr|Lys|Val|Asp|Lys|Arg|Val|Glu|Pro|Lys|Ser|
| |210| | | |215| | | |220| | | | | | |
|Cys|Asp|Lys|Thr|His|Thr|Cys|Pro|Pro|Cys|Pro|Ala|Pro|Glu|Leu|Leu|
|225| | | |230| | | |235| | | | | | |240|
|Gly|Gly|Pro|Ser|Val|Phe|Leu|Phe|Pro|Pro|Lys|Pro|Lys|Asp|Thr|Leu|
| | | |245| | | |250| | | |255| | | | |
|Met|Ile|Ser|Arg|Thr|Pro|Glu|Val|Thr|Cys|Val|Val|Val|Asp|Val|Ser|
| | | |260| | | |265| | | |270| | | | |
|His|Glu|Asp|Pro|Glu|Val|Lys|Phe|Asn|Trp|Tyr|Val|Asp|Gly|Val|Glu|
| |275| | | |280| | | |285| | | | | | |
|Val|His|Asn|Ala|Lys|Thr|Lys|Pro|Arg|Glu|Glu|Gln|Tyr|Asn|Ser|Thr|
| |290| | | |295| | | |300| | | | | | |
|Tyr|Arg|Val|Val|Ser|Val|Leu|Thr|Val|Leu|His|Gln|Asp|Trp|Leu|Asn|
|305| | | |310| | | |315| | | | | | |320|
|Gly|Lys|Glu|Tyr|Lys|Cys|Lys|Val|Ser|Asn|Lys|Ala|Leu|Pro|Ala|Pro|
| | | |325| | | |330| | | |335| | | | |
|Ile|Glu|Lys|Thr|Ile|Ser|Lys|Ala|Lys|Gly|Gln|Pro|Arg|Glu|Pro|Gln|
| | | |340| | | |345| | | |350| | | | |
|Val|Tyr|Thr|Leu|Pro|Pro|Ser|Arg|Glu|Glu|Met|Thr|Lys|Asn|Gln|Val|
| | | |355| | | |360| | | |365| | | | |
|Ser|Leu|Thr|Cys|Leu|Val|Lys|Gly|Phe|Tyr|Pro|Ser|Asp|Ile|Ala|Val|
| | | |370| | | |375| | | |380| | | | |
|Glu|Trp|Glu|Ser|Asn|Gly|Gln|Pro|Glu|Asn|Asn|Tyr|Lys|Thr|Thr|Pro|
|385| | | |390| | | |395| | | | | | |400|
|Pro|Val|Leu|Asp|Ser|Asp|Gly|Ser|Phe|Phe|Leu|Tyr|Ser|Lys|Leu|Thr|
| | | |405| | | |410| | | |415| | | | |
|Val|Asp|Lys|Ser|Arg|Trp|Gln|Gln|Gly|Asn|Val|Phe|Ser|Cys|Ser|Val|
| | | |420| | | |425| | | |430| | | | |
|Met|His|Glu|Ala|Leu|His|Asn|His|Tyr|Thr|Gln|Lys|Ser|Leu|Ser|Leu|
| | | |435| | | |440| | | |445| | | | |
|Ser|Pro|Gly|Lys| | | | | | | | | | | | |
| | | |450| | | | | | | | | | | | |

<210> SEQ ID NO 21
<211> LENGTH: 642
<212> TYPE: DNA
<213> ORGANISM: Artificial
<220> FEATURE:
<223> OTHER INFORMATION: The nucleotide sequence of the light chain of
      the antibody MA-042

<400> SEQUENCE: 21
gacatacaga tgactcaaag cccttattcg ctcagtgcgt cggtcgggga cagagtaacc        60
atcacctgca aggcgtcaaa gtcaatcaat aagtatctgg cgtggttcca gcagaagcca      120
ggaaagccta acaagctatt aatatacgat gggtctaccc tccaatccgg ggtcccttca      180

```
cgattttctg gaagcggctc aggaaccgat tcacgctga ccatcagtag cttggagcct      240
gaggactttg ccacttatta ttgccagcag cacaacgagt atcctcccac cttcggacag      300
ggtacaaaac tggagatcaa gcgtacggtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gt                        642
```

<210> SEQ ID NO 22
<211> LENGTH: 214
<212> TYPE: PRT
<213> ORGANISM: Artificial
<220> FEATURE:
<223> OTHER INFORMATION: The amino acid sequence of a light chain of the antibody MA-042

<400> SEQUENCE: 22

```
Asp Ile Gln Met Thr Gln Ser Pro Tyr Ser Leu Ser Ala Ser Val Gly
1               5                   10                  15

Asp Arg Val Thr Ile Thr Cys Lys Ala Ser Lys Ser Ile Asn Lys Tyr
            20                  25                  30

Leu Ala Trp Phe Gln Gln Lys Pro Gly Lys Pro Asn Lys Leu Leu Ile
        35                  40                  45

Tyr Asp Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln His Asn Glu Tyr Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

MONOCLONAL ANTIBODIES THAT BIND SPECIFICALLY TO HUMAN TRBV9

FIELD OF THE INVENTION

The invention relates to the field of biotechnology and biomedicine, in particular to antibodies or antigen-binding fragments thereof, as well as to use thereof. More specifically, the present invention relates to a monoclonal humanized antibody that specifically binds to a human T cell receptor family. The invention also relates to a nucleic acid encoding said antibody or antigen-binding fragment thereof, an expression vector, a method for preparing said antibody, and use of said antibody in treatment of diseases or disorders associated with the human T cell receptor family.

BACKGROUND OF THE INVENTION

Autoimmune diseases are caused by autoreactive T lymphocytes (Haroon N et al., Arthritis Rheum. 2013 October; 65(10):2645-54, Duarte J. et al., PloS One 2010 May 10; 5(5):e10558; Konig M. et al., Front Immunol 2016 Jan. 25; 7:11). The prior art discloses that a T cell receptor (TCR) sequence is a marker allowing to identify a T-lymphocytes clone involved in the pathogenesis of an autoimmune disease. Structurally, the subunits of T-cell receptors are members of the immunoglobulin superfamily and are formed from several gene segments. The TCR variable regions form the TCR antigen-binding site. This means that they are clone-specific, i.e. differ in T lymphocytes that respond to distinct antigens.

In terms of the amino acid homology of variable (V) gene segments within the TCR variable domain, T cell receptors are divided into different families. According to the IMGT nomenclature, the beta-chain is distinguished into 26 distinct families, and the alpha chain is distinguished into 41 families (Turner S J et al., Nature Reviews Immunology 2006, V.6, 883-894). To determine the TCR chain family, one uses multiple alignment of a test amino acid sequence and known TCR chain sequences, the information on which is summarized in the IMGT database ("The international ImMunoGeneTics information system", Lefranc M-P., Nucl Acids Res 2001; 29:207-209) available on the Internet at http://www.imgt.org. Multiple alignment and determination of a TCR chain family can be performed using IgBlast software package.

WO9006758 discloses monoclonal antibodies W112 and 2D1 to β-chain regions of the human T cell receptor variable domains, which belong to the TRBV5-3 and TRBV8-1 families, proposed as a means for diagnosis and therapy of rheumatoid arthritis. Said monoclonal antibodies recognize between 0.3 to 5% of peripheral T lymphocytes bearing TRBV5-3 and 0.5 to 13% of peripheral T lymphocytes bearing TRBV8-1, respectively. The results of many studies demonstrating the involvement of T lymphocytes in the pathogenesis of rheumatoid arthritis gave rise to the use of monoclonal antibodies specific for T receptors' beta-chain regions. In particular, Brennan et al., Clin Exp Immunol. 1988 September; 73(3): 417-423 has demonstrated elevated percentage of T lymphocytes bearing TRBV5 and TRBV8 in synovial samples of patients suffering from rheumatoid arthritis as compared to healthy ones. WO9405801 discloses monoclonal antibodies for diagnosis and therapy of rheumatoid arthritis interacting with an epitope of the VB3.1 variable region of the human T-cell receptor, which interact with the TCR V(beta)3.1 subfamily.

Monoclonal antibodies that specifically recognize the 13th family beta-chain of the rat TRC have also been described Animal models has demonstrated that, with the help of these antibodies, it is possible to preventively remove a small population of T cells, the T receptor of which comprises VB13 beta-chain (VB13+ T cells), and it has been shown that such procedure protects against the development of type I diabetes in rats of diabetes-prone line, and also significantly reduces the risk of development of virus-induced diabetes (Zhijun Liu et al., Diabetes. 2012 May; 61(5): 1160-1168.). At the same time, the result of removal of T cells, the T receptor of which comprises a distinct beta-chain family (VB16), does not differ from that of control groups. It is important to note that even the first administration of a monoclonal antibody against VB13 results in a 60% decrease in the number of VB13+ T cells in the rat spleen.

A consensus variant of autoimmune TCRs in patients with ankylosing spondylitis (AS or Bekhterev's disease) has been described, it has been shown that it is present in synovial fluid and peripheral blood in patients with AS and absent at the same depth of analysis in healthy donors, regardless of their HLA*B27 allele status (Faham M. et al., Arthritis Rheumatol. 2017; 69(4):774-784; Komech E et al. 12th EJI-EFIS Tatra Immunology Conference; 2016 Sep. 3-7; Strbske Pleso, Slovakia. Abstract book p. 39). Said TCRs are members of the TRBV9 family (according to the IMGT nomenclature). It has been shown that T cell receptors bearing TRBV9 family beta-chains are also involved in the development of such an autoimmune disease as celiac disease (Petersen J et al., J Immunol. 2015; 194(12): 6112-22). They are also found on the surface of T cells subject to malignization in T cell lymphomas and T cell leukemias, including T-cell lymphoma caused by the Epstein-Barr virus (EBV) (Toyabe S et al., Clin Exp Immunol. 2003; 134(1): 92-97).

Application No. RU2017145662 has recently described chimeric monoclonal antibodies able to specifically bind to the TRBV9 family beta-chain region of the human T receptor, which can be used in therapy of autoimmune and oncological diseases, the pathogenesis of which involves TCRs belonging to the TRBV9 family, for example, AS, celiac disease and some T cell lymphomas and T cell leukemias.

Said antibodies are the only currently known antibodies that can be used to eliminate T cells bearing the TRBV9 family TCRs. The main disadvantage of said antibodies is a relatively low degree of humanization, i.e. they comprise human-like constant regions and structural components, but have a rat-like variable domain. The degree of humanization of the variable fragment of heavy chain of said antibodies is 72%, whereas that of the variable fragment of light chain is 69%.

The above parental monoclonal antibody includes:
1) a variable domain of their heavy chain (VH), which comprises 3 hypervariable regions, HCDR1, HCDR2 and HCDR3, wherein
   HCDR1 (according to the Kabat numbering scheme) has the amino acid sequence of SEQ ID NO: 1,
   HCDR2 has the amino acid sequence of SEQ ID NO: 2
   HCDR3 has the amino acid sequence of SEQ ID No 3;
2) a variable domain of their light chain (VL), which comprises 3 hypervariable regions, LCDR1, LCDR2 and LCDR3, wherein:
   LCDR1 has the amino acid sequence of SEQ ID NO: 4,
   LCDR2 has the amino acid sequence of SEQ ID NO: 5,
   LCDR3 has the amino acid sequence of SEQ ID NO: 6.

The above parental monoclonal antibody includes the variable domains of heavy and light chains, which have the amino acid sequences shown in SEQ ID NOs: 8 and 10.

The above parental monoclonal antibody includes a light chain, which has the amino acid sequence shown in SEQ ID No. 12, and an antibody heavy chain, which has the amino acid sequence of SEQ ID No. 14.

Examples of nucleotide sequences encoding said amino acid sequences of heavy and light chains of the above parental antibody are shown in SEQ ID NOs: 13 and 11.

The invention is directed to the generation of a monoclonal antibody, which can be used to eliminate T cells bearing the TRBV9 family TCRs, in particular for the therapy of AS, celiac disease and malignant blood diseases, the pathogenesis of which involves the TRBV9 family TCRs, and which is characterized by a high degree of humanization. At the same time, humanization often leads to a critical decrease in antibody affinity and/or solubility. Thus, it is a relevant task to generate humanized functional antibodies.

BRIEF SUMMARY OF THE INVENTION

The present invention relates to a humanized monoclonal antibody and antigen-binding fragment thereof, which have the ability to specifically bind with high affinity to the TRBV9 family beta-chain region of the human T receptor. An antibody according to the invention can be used as a medicine for treating autoimmune and oncological diseases, the pathogenesis of which involves TCRs belonging to the TRBV9 family, for example, AS, celiac disease and some T cell lymphomas and T cell leukemias.

In preferred embodiments, an antibody of the present invention comprises a variable domain of heavy chain (VH) with three hypervariable regions
1) HCDR 1 (according to the Kabat numbering scheme) has the amino acid sequence of SEQ ID NO: 1,
2) HCDR 2 has the amino acid sequence of SEQ ID NO: 2
3) HCDR 3 has the amino acid sequence of SEQ ID No 3;
2) a variable domain of light chain (VL) with three hypervariable regions, LCDR1, LCDR2 and LCDR3, wherein:
LCDR 1 has the amino acid sequence of SEQ ID NO: 4,
LCDR 2 has the amino acid sequence of SEQ ID NO: 5,
LCDR 3 has the amino acid sequence of SEQ ID NO: 6.

Unless specifically stated otherwise, the well-known Kabat numbering scheme is used hereinafter to determine the CDRs of antibodies.

Thereby, antibody heavy and light chain variable domains comprise amino acid substitutions in the FR fragments of the heavy and light chain variable domains, which increase the degree of humanization of the antibody as compared to the parental one.

In some embodiments, the variable domain of heavy chain of an antibody of the present invention comprises at least 10 humanizing amino acid substitutions as compared to the variable domain of heavy chain of the parental antibody, the amino acid sequence of which is shown in SEQ ID No 8.

In preferred embodiments, the variable domain of heavy chain of an antibody of the present invention has the sequence shown in SEQ ID No: 16.

In some embodiments, the variable domain of heavy chain of an antibody of the present invention comprises further amino acid substitutions that do not alter antibody specificity.

In some embodiments, the variable domain of light chain of an antibody of the present invention comprises at least 10 humanizing amino acid substitutions as compared to the variable domain of light chain of the parental antibody, the amino acid sequence of which is shown in SEQ ID No 10.

In preferred embodiments, the variable domain of light chain of an antibody of the present invention has the sequence shown in SEQ ID NO 18.

In some embodiments, the variable domain of light chain of an antibody of the present invention comprises further amino acid substitutions that do not alter antibody specificity.

In some embodiments, monoclonal antibodies of the invention are full-length human IgG antibodies, for example, IgG1 or IgG2 or IgG3 or IgG4.

In some embodiments, an antibody of the invention includes a heavy chain, the amino acid sequence of which is at least 85% identical, or at least 90% identical, or at least 91% identical, or at least 92%, or at least 93% identical, or at least 94%, or at least 95%, or at least 96%, or at least 97%, or at least 98% or at least 99% or 100% identical to the amino acid sequence of SEQ ID NO: 20.

In some embodiments, an antibody of the invention includes a light chain, the amino acid sequence of which is at least 85% identical, or at least 90% identical, or at least 91% identical, or at least 92%, or at least 93% identical, or at least 94%, or at least 95%, or at least 96%, or at least 97%, or at least 98% or at least 99% or 100% identical to the amino acid sequence of SEQ ID NO: 22.

In some embodiments, an antibody has a light chain, the amino acid sequence of which is shown in SEQ ID NO: 22, and a heavy chain, the amino acid sequence of which is shown in SEQ ID NO: 20.

Also provided are nucleic acids that encode the variable domains of heavy and light chain of an antibody according to the invention, nucleic acids encoding the heavy and light chains of antibodies according to the invention and functional fragments thereof.

Also provided are expression cassettes and expression vectors including a nucleic acid of the present invention and regulatory elements necessary for expression of the nucleic acid in a selected host cell. The vector or expression cassette may be present in the host cell as an extrachromosomal element or integrated into the cell genome as a result of introduction (by transfection) of said expression cassette or vector into the cell.

Furthermore, provided are cells and stable cell lines including nucleic acids, vectors or expression cassettes of the present invention, and methods for preparation thereof.

Also provided is a method for producing the above antibody or antigen-binding fragment thereof, comprising culturing the above host cell in a culture medium under conditions ensuring production of said antibody. In some embodiments, a method includes subsequent isolation and purification of the resulting antibody.

Also provided is a pharmaceutical composition for preventing or treating a disease or disorder mediated by the TRBV9 family beta-chain region of the human T receptor, comprising the above antibody or antigen-binding fragment thereof in combination with one or more pharmaceutically acceptable excipients.

In one of embodiments, a pharmaceutical composition is intended to prevent or treat a disease or disorder selected from the group: ankylosing spondylitis, celiac disease, T cell leukemia, T cell lymphoma.

Also provided is a pharmaceutical combination for preventing or treating a disease or disorder mediated by the human T cell receptor bearing the TRBV9 family beta-chain, comprising the above antibody or antigen-binding fragment thereof and at least one other therapeutically active compound.

In one of embodiments, a pharmaceutical combination is intended to prevent or treat a disease or disorder selected from the group: ankylosing spondylitis, celiac disease, T cell leukemia, T cell lymphoma.

In one embodiment, a pharmaceutical combination or composition comprises other therapeutically active compound that is selected from a small molecule, antibody or steroid hormones, such as corticosteroids.

Also provided is a method for inhibiting the biological activity of the T cell receptor, the beta-chain of which belongs to the TRBV9 family, in a subject in need of such inhibition, comprising administering to the subject an effective amount of the above antibody or antigen-binding fragment thereof.

Also provided is a method for treating a disease or disorder mediated by the human T cell receptor bearing the TRBV9 family beta-chain, comprising administering to a subject in need of such treatment the above antibody or antigen-binding fragment thereof or said pharmaceutical composition, in a therapeutically effective amount.

In one of embodiments of the method for treating a disease or disorder, the disease or disorder is selected from the group: ankylosing spondylitis, celiac disease, T cell leukemia, T cell lymphoma.

Also provided is use of the above antibody or antigen-binding fragment thereof or the above pharmaceutical composition for treating in a subject in need of such treatment a disease or disorder mediated by the human T cell receptor bearing the TRBV9 family beta-chain.

In one of embodiments of use, the disease is selected from the group: ankylosing spondylitis, celiac disease, T cell leukemia, T cell lymphoma.

The technical result of the present invention consists in obtaining antibodies with a high degree of humanization, which specifically bind with high affinity to TCRs, the beta-chain of which belongs to the TRBV9 family, and can be used to treat autoimmune and oncological diseases, the pathogenesis of which involves TCRs, the beta-chain of which belongs to the TRBV9 family.

In preferred embodiments, an antibody heavy chain variable fragment is characterized by a degree of humanization of 87%. In preferred embodiments, an antibody light chain variable fragment is characterized by a degree of humanization of 85%.

DETAILED DESCRIPTION OF THE INVENTION

Figure 1:
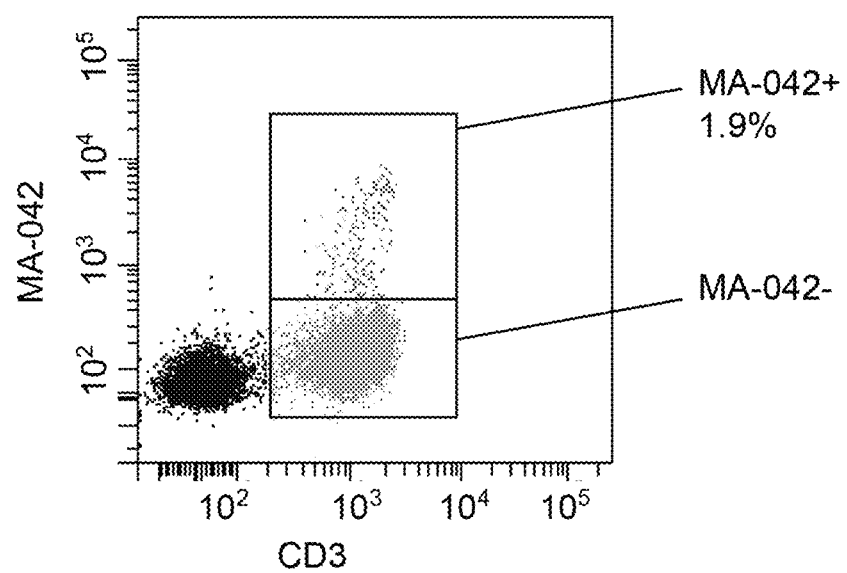
FIG. 1 shows the result of sorting T lymphocytes using antibody MA-042.

The present invention relates to isolated monoclonal antibodies and functional fragments thereof having the ability to specifically bind to the TRBV9 family beta-chain region of the human T receptor, with an increased degree of humanization relative to analogues. Also provided are nucleic acids encoding antibodies and fragments thereof of the invention, expression cassettes and expression vectors including a nucleic acid of the present invention and regulatory elements necessary for expression of the nucleic acid in a selected host cell. Furthermore, provided are cells and stable cell lines including nucleic acids, vectors or expression cassettes of the present invention. Also provided are a method for producing a monoclonal antibody or a functional fragment thereof, a pharmaceutical composition and a pharmaceutical combination comprising in an effective amount an antibody of the present invention in combination with one or more pharmaceutically acceptable excipients, diluents or carriers, and methods for diagnosis and therapy of AS and other diseases using antibodies of the present invention.

Definitions

The invention will be easier understood with definition of some terms first.

It is understood that the materials and methods provided herein are not limited to particular compositions and method steps, as these may vary. It must be noted that as used herein and in the appended claims, the singular forms include the corresponding plural reference unless the context clearly dictates otherwise.

Human "T cell receptor", also referred to as "TCR", "T receptor", is a heterodimeric protein complex found on the surface of a T lymphocyte. The T receptor is present only on T lymphocytes. The main function of TCR is to specifically recognize processed antigens bound to the molecules of major histocompatibility complex (HLA).

Human TCR consists of two subunits, α and β chains, or γ and δ chains, connected through a disulfide bond and docked onto the cell membrane. Each of the TCR chains has an N-terminal variable (V) domain, a connecting domain, and a constant (C) domain connected to a transmembrane domain that anchors the receptor in the T lymphocyte plasma membrane. The length of the constant domain of alpha and beta-chains is 91 and 129 amino acid residues, respectively. The length of the connecting and transmembrane domain of the alpha chain is 30 and 17 amino acid residues (AARs), and that of the beta-chain is 21 and 22 AARs. The length of T receptors variable domains varies from 104 to 125 AARs.

A small fraction of T lymphocytes has the γ/δ type T receptors. They are arranged similar to the α/β receptors, but differ in their primary structure and have a number of functional features. They exhibit a much lower variability (limited clone specificity), they recognize antigens in the complex with "non-classical" (non-MHC) antigen-presenting molecules or even free antigens.

The T receptor reacts with the MHC/antigen complex via six regions determining complementarity thereof (CDRs): three alpha chain regions and three beta-chain regions. These CDRs are hypervariable regions, the loops of variable domains of the T cell receptor, Valfa and Vbeta.

The terms "TRBV9" or "TRBV9 family" refer to the ninth family of beta-chains of T cell receptors, as distinguished according to the IMGT nomenclature, which is characterized in that the amino acid sequence of variable domain thereof comprises unique motifs of CDR1 (amino acid sequence is S-G-D-L-S) and CDR2 (amino acid sequence is Y-Y-N-G-E-E). The term "TRBV9 family TCR" refers to a T cell receptor, the beta-chain of which belongs to the TRBV9 family.

The term "pathological" in relation to T lymphocytes or TCRs means that such TCR or a TCR-bearing T lymphocyte are associated with a disease or pathology and/or cause a disease and/or contribute to the development of a disease.

The term "autoimmune" in relation to TCR means that such TCR is involved in the development of an autoimmune disease.

The term "antibody" as used herein is intended to refer to an immunoglobulin molecule consisting of four polypeptide chains (two heavy (H) chains and two light (L) chains) linked by disulfide bonds. Light chains are classified as kappa or lambda. Heavy chains are classified as gamma, mu, alfa, delta or epsilon; they determine the antibody isotype such as IgG, IgM, IgA, IgD and IgE respectively, and several of them can be further divided into subclasses (isotypes), for example IgG1, IgG2, IgG3, IgG4, IgA1 and IgA2. Each heavy chain type is characterized by a specific constant region.

Each heavy chain comprises a heavy chain variable region (herein abbreviated as HCVR or VH) and a heavy chain constant region. The heavy chain constant region comprises three domains, CH1, CH2, and CH3. Each light chain comprises a light chain variable region (herein abbreviated as LCVR or VL) and a light chain constant region. The light chain constant region comprises one domain, CL. The VH and VL regions can be further subdivided into regions of hypervariability, termed complementarity determining regions (CDRs), surrounded by regions that are more conserved, termed framework regions (FRs). Each VH and VL is composed of three CDRs and four FRs, arranged from amino-terminus to carboxy-terminus in the following order: FR1, CDR1, FR2, CDR2, FR3, CDR3, FR4.

In the present application, 3 heavy chain CDRs are referred to as "HCDR1, HCDR2 and HCDR3", whereas 3 light chain CDRs are referred to as "LCDR1, LCDR2 and LCDR3". The CDRs contain most of the residues that specifically interact with the antigen. CDR-amino residues within HCVRs and LCVRs of antibodies according to the present invention are numbered and positioned in compliance with the well-known Kabat numbering scheme, unless otherwise stated. The present application includes the conventional letter codes for amino acids, unless otherwise stated.

The terms "anti-TRBV9 antibody", "antibody to TRBV9", "antibody specifically binding to the TRBV9 family beta-chain" and "antibody against the TRBV9 family beta-chain" are interchangeable in the context of the present application and relate to an antibody that specifically binds to the epitope of TRBV9 family beta-chain of the human T cell receptor.

In addition, "monoclonal antibody" as used in the present application can be a single-chain Fv-fragment which can be obtained by binding LCVR- and HCVR-encoding DNA to a linker sequence (see Pluckthun, The Pharmacology of Monoclonal Antibodies, vol. 113, Rosenburg and Moore eds., Springer-Verlag, New York, p. 269-315, 1994). It is contemplated that regardless of whether fragments or portions are mentioned, the term "antibody" as used in the present application includes such fragments or portions as well as single-chain forms. As long as the protein keeps its ability of specific or preferable binding the target thereof (for example, epitope or antigen), it is covered by the term "antibody". Antibodies can be either glycosylated or not and still are within the scope of the invention.

The terms "antibody" and "monoclonal antibody" for the purposes of the present application refer to a monoclonal antibody against the TRBV9 family TCR. As used herein, "monoclonal antibody" relates to an antibody of rodents, primates or Camelidae family, preferably to murine, monkey, camel or llama antibody, chimeric antibody, humanized antibody or fully human antibody, unless otherwise stated.

The population of "monoclonal antibodies" refers to a homogenous or substantially homogeneous antibody population (i.e. at least about 85, 90, 91, 92, 93, 94, 95, 96%, more preferably at least about 97 or 98%, or even more preferably at least 99% of antibodies in the population will compete for the same antigen/epitope in ELISA, or more preferably antibodies are identical in terms of their amino acid sequences). Antibodies can be either glycosylated or not, yet still be within the scope of the invention. Monoclonal antibodies may be homogenous if they have an identical amino acid sequence, although they can differ in post-translation modification, for example, a glycosylation pattern.

Variable regions of each pair light/heavy chain form antigen-binding sites of an antibody. As used in this application, an "antigen binding part", or "antigen binding region", or "antigen binding domain" or "antigen-binding site" interchangeably relate to such part of an antibody molecule which comprises amino acid residues which interact with the antigen and give the antibody specificity and affinity in relation to the antigen. This part of an antibody includes "framework" amino acid residues needed to maintain appropriate conformation of antigen-binding residues.

The term "human antibody", as used herein, refers to an antibody, in which the sequences of variable and constant domains are derived from human sequences. Human antibodies according to the invention may include amino acid residues that are not typical of human (for example, mutations introduced by in vitro undirected or site-specific mutagenesis or in vivo somatic mutation), for example, in CDR, and particularly, in CDR3.

The term "humanized", when used in reference to antibodies, is used to refer to antibodies that are characterized by the presence of human-like constant regions and structural components, but have complementarity determining regions (CDRs) that are typical of immunoglobulins of other origin, or of corresponding fragments of modified antibodies.

A "parental" antibody, as used in this application, is an antibody encoded by an amino acid sequence that is used for obtaining a variant. Parental antibody can be from rodent, llama, chimeric, humanized or human antibody.

The term "degree of humanization" in relation to antibodies is used to refer to the percent identity of a humanized antibody's framework region sequence with an original human acceptor framework region that was used to generate the humanized antibody and that is obtainable from a human library. Preferably, an antibody of the invention comprises a framework region having at least 80% identity, typically at least 82%, more often at least 83%, for example, at least 84%, or at least 85%, or at least 86%, or at least 87% identity in relation to the framework region obtained from the human library.

The term "humanizing substitutions" refers to amino acid substitutions that increase the degree of humanization of an antibody or fragment thereof.

The term "chimeric" in reference to antibodies of the present invention is used to refer to antibodies that are characterized by human-like constant regions but have variable regions of other origin. In such antibodies, the variable domains of light and/or heavy chains of non-human origin (for example, of rat origin) are operatively linked to the constant domains of the corresponding chains of human origin.

The term "operatively linked" or the like, when used to describe antibodies, refers to polypeptide sequences that are placed in a physical (covalent, unless stated otherwise) and functional relationship to each other. In the most preferred embodiments, the functions of the polypeptide components of the chimeric molecule are unchanged as compared to the functional properties of isolated polypeptide components. The term "operatively linked" or the like, when used to describe nucleic acids, means that the nucleic acids are covalently linked so that no reading frame shifts and stop codons are present at the points where they are linked. As is obvious to those skilled in the art, nucleotide sequences encoding a chimeric protein comprising "operatively linked" components (proteins, polypeptides, linker sequences, protein domains, etc.) consist of fragments encoding said components, wherein said fragments are covalently linked so that a full-length chimeric protein, for example, a chimeric antibody according to the invention, is produced during translation and transcription of the nucleotide sequence.

As used herein, the term "isolated" means a molecule or a cell that are in an environment different from the environment in which the molecule or cell is in vivo.

In preferred embodiments, antibodies of the present invention are recombinant, i.e. obtained using the recombinant DNA technique. The term "recombinant antibody", as used herein, includes all antibodies that are obtained, expressed, created or isolated by recombinant means, such as antibodies expressed using a recombinant expression vector introduced into a host cell, antibodies isolated from a set of known recombinant, combinatorial human antibody library, antibodies isolated from an animal that is transgenic for human immunoglobulin genes (see, e.g., Taylor L. D. et al. (1992) Nucl. Acids Res. 20:6287-6295). In some embodiments, the recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, cannot naturally exist within the human antibody germline repertoire in vivo.

The term "specifically binds" as used in this application refers to the situation in which one member of a specific binding pair does not significantly bind to molecules other than specific binding partner(s) thereof. The term is also applicable where e.g. an antigen-binding domain of an antibody of the invention is specific for a particular epitope that is carried by a number of antigens; in this case, the specific antibody comprising the antigen-binding domain will be able to specifically bind to various antigens carrying the epitope. Accordingly, a monoclonal antibody of the invention specifically binds the epitope of TRBV9 family beta-chain of the human T cell receptor, whereas it does not specifically bind the TCR beta-chains of other families and TCR alpha chains.

The term "epitope" refers to that part of a molecule capable of being recognized by and bound by an antibody at one or more of the antibody's antigen-binding regions. Epitopes often consist of a chemically active surface grouping of molecules such as amino acids or sugar side chains and have specific three-dimensional structural characteristics as well as specific charge characteristics.

As used herein, the term "epitope", inter alia, refers to a polypeptide fragment, having antigenic and/or immunogenic activity in an animal, preferably in a mammal, for example a mouse, rat or human. The term "antigenic epitope" as used in this application is a polypeptide fragment which can specifically bind the antibody and can be detected by any technique well known from the prior art, for example, by the standard immunoassay. Antigen epitopes are not necessarily immunogenic, however, they can be immunogenic. "Immunogenic epitope" as used herein is defined as a polypeptide fragment that evokes an antibody response in animals, as determined by any method known from the prior art. "Nonlinear epitope" or "conformational epitope" comprise nonadjacent polypeptides (or amino acids) within an antigen protein that binds to epitope-specific antibody.

The phrases "biological property" or "biological characteristic", or the terms "activity" or "bioactivity" in reference to an antibody or functional fragments thereof of the present invention are used interchangeably in this application and include, but are not limited to, epitope/antigen affinity and specificity, ability to neutralize or antagonize the activity of TCR that includes the beta-chain belonging to the TRBV9 family.

Other identifiable biological properties of an antibody include, for example, cross-reactivity, (i.e., with non-human homologs of a target peptide, or with other proteins or tissues, generally), and ability to preserve high levels of expression of protein in mammalian cells. The aforementioned properties or characteristics can be observed, measured, and/or assessed using techniques recognized in the art including, but not limited to, ELISA, competitive ELISA, BIACORE or KINEXA surface plasmon resonance analysis, in vitro or in vivo inhibition assays without limitation, receptor binding assays, cytokine or growth factor production and/or secretion assays, and signal transduction and immunohistochemistry of tissue sections obtained from various sources, including human, primate or any other source.

The terms "inhibit" or "neutralize" as used in this application with respect to the activity of an antibody of the invention refer to the ability to substantially antagonize, prohibit, prevent, restrain, slow, disrupt, eliminate, stop, reduce, for example progression or severity of that which is being inhibited including, but not limited to the above, the biological activity of antibody, or property, disease or condition.

As used herein, the term "mutant" or "variant" refers to an antibody disclosed in the present invention, in which one or more amino acids are added and/or substituted and/or deleted and/or inserted at the N-terminus and/or C-terminus and/or within the native amino acid sequences of antibodies of the present invention or fragments thereof. As used herein, the term "mutant" also refers to a nucleic acid molecule that encodes a mutant protein. Furthermore, the term "mutant" refers to any variant that is shorter or longer than the protein or nucleic acid.

The term "homology" is used to describe the relationship of nucleotide or amino acid sequences with other nucleotide or amino acid sequences, which is determined by the degree of identity and/or similarity between said sequences being compared.

As used herein, an amino acid or nucleotide sequence are "substantially similar" or "substantially the same" as a reference sequence if the amino acid or nucleotide sequence has at least 85% identity with a specified sequence within a region selected for comparison. Thus, substantially similar sequences include those that have, for example, at least 90% identity, or at least 91% identity, or at least 92% identity, or at least 93% identity, or at least 94% identity, or at least 95% identity, or at least 96% identity, or at least 97% identity, or at least 98% identity, or at least 99% identity. Two sequences that are identical to one another are also substantially similar.

Sequence identity is determined based on a reference sequence. Algorithms for sequence analysis are known in the art, such as IgBLAST described in Ye et al. Nucleic Acids Res. 2013, W34-40. For the purposes of the present invention, to determine the level of identity and similarity between nucleotide sequences and amino acid sequences, the nucleotide and amino acid sequences can be compared with the help of IgBLAST software package provided by the National Center for Biotechnology Information (https://www.ncbi.nlm.nih.gov/igblast/) using gapped alignment with standard parameters. To calculate the percent identity, the full length of a reference sequence, for example, a variable region, is used.

A reference to a nucleotide sequence "encoding" polypeptide means that the polypeptide is produced from the nucleotide sequence during translation and transcription of mRNA. Thereby, both a coding chain identical to mRNA and typically used in the list of sequences and a complementary chain that serves as a template for transcription can be indicated. As is obvious to those skilled in the art, the term also includes any degenerate nucleotide sequences encoding the same amino acid sequence. Nucleotide sequences encoding a polypeptide include sequences comprising introns.

Antibodies

As mentioned above, the present invention relates to isolated monoclonal humanized antibodies and functional fragments thereof having the ability to specifically bind to the TRBV9 family beta-chain region of the human T receptor.

Antibodies according to the invention can be chimeric, humanized or human antibodies, or antigen-binding fragments thereof, and can be used as a medicine for treating AS and other diseases, the pathogenesis of which involves TCRs belonging to the TRBV9 family, for example, celiac disease or T cell lymphoma.

An antibody according to the invention is monoclonal. Monoclonal antibodies of the invention can be produced using, for example, hybridoma techniques well known in the art, as well as recombinant technologies, phage display technologies, synthetic technologies or combinations of such technologies or other technologies well known in the art. The term "monoclonal antibody" as used in this application refers to an antibody obtained from a single copy or a clone including, for example, any eukaryotic, prokaryotic or phage clone, rather than to production method thereof.

Humanized and chimeric antibodies can be generated by peptide synthesis or using recombinant DNA techniques as described in the "Nucleic acids" section below.

In some embodiments, antibodies of the present invention are chimeric and characterized in that they have variable domains of light and heavy chains of non-human origin (for example, of rat or murine origin), and human origin constant domains.

An antibody of the present invention comprises a variable domain of heavy chain (VH) with three hypervariable regions
1) HCDR1 (according to the Kabat numbering scheme) has the amino acid sequence of SEQ ID NO: 1,
2) HCDR2 has the amino acid sequence of SEQ ID NO: 2
3) HCDR3 has the amino acid sequence of SEQ ID No 3;
2) a variable domain of light chain (VL) with three hypervariable regions, LCDR1, LCDR2 and LCDR3, wherein:
LCDR 1 has the amino acid sequence of SEQ ID NO: 4,
LCDR 2 has the amino acid sequence of SEQ ID NO: 5,
LCDR 3 has the amino acid sequence of SEQ ID NO: 6.

Unless specifically stated otherwise, the well-known Kabat numbering scheme is used hereinafter to determine the CDRs of antibodies.

In all embodiments, the variable domains of light and heavy chain of an antibody of the present invention are humanized and different from those of the parental antibody in humanizing amino acid substitutions, wherein the variable domains of heavy and light chain of the antibody comprise amino acid substitutions in the FR fragments of the variable domains of heavy and light chain, increasing the degree of humanization of the antibody as compared to the parental one.

In some embodiments, the variable domain of heavy chain of an antibody of the present invention comprises at least 10 humanizing amino acid substitutions as compared to the variable domain of heavy chain of the parental antibody, the amino acid sequence of which is shown in SEQ ID No 8.

In preferred embodiments, the variable domain of heavy chain of an antibody of the present invention has the amino acid sequence shown in SEQ ID No: 16.

In some embodiments, the variable domain of heavy chain of an antibody of the present invention comprises further amino acid substitutions that do not alter antibody specificity.

In some embodiments, the variable domain of light chain of an antibody of the present invention comprises at least 10 humanizing amino acid substitutions as compared to the variable domain of light chain of the parental antibody, the amino acid sequence of which is shown in SEQ ID No 10.

In preferred embodiments, the variable domain of light chain of an antibody of the present invention comprises amino acid substitutions and has the sequence shown in SEQ ID NO 18.

In some embodiments, the variable domain of light chain of an antibody of the present invention comprises further amino acid substitutions that do not alter antibody specificity.

In some embodiments, monoclonal antibodies of the invention are full-length human IgG antibodies, for example, IgG1 or IgG2 or IgG3 or IgG4.

In some embodiments, an antibody of the invention includes a heavy chain, the amino acid sequence of which is at least 85% identical, or at least 90% identical, or at least 91% identical, or at least 92%, or at least 93% identical, or at least 94%, or at least 95%, or at least 96%, or at least 97%, or at least 98% or at least 99% or 100% identical to the amino acid sequence of SEQ ID NO: 20.

In some embodiments, an antibody of the invention includes a light chain, the amino acid sequence of which is at least 85% identical, or at least 90% identical, or at least 91% identical, or at least 92%, or at least 93% identical, or at least 94%, or at least 95%, or at least 96%, or at least 97%, or at least 98% or at least 99% or 100% identical to the amino acid sequence of SEQ ID NO: 22.

In some embodiments, an antibody has a light chain, the amino acid sequence of which is shown in SEQ ID NO: 22, and a heavy chain, the amino acid sequence of which is shown in SEQ ID NO: 20.

As is known from the prior art, mutations can be introduced into antibody sequences, including variable domains, which do not substantially alter the antibody ability to bind to an antigen. Antibodies according to the present invention may also contain further mutations that do not lead to a loss in the antibody ability to bind the TRBV9 family beta-chain of TCR, but can lead to a decrease in antibody-dependent cell-mediated cytotoxicity or an increase in affinity or other biological properties of antibodies. In particular, it is well known from the prior art, conservative amino acid substitutions can be made in an antibody sequence. "Conservative substitution" in the context of this application refers to a substitution in which an amino acid residue is replaced by another amino acid residue having a similar side chain. Families of the amino acid residues having the similar side chains are well-known in the art, which include basic side chains (e.g., lysine, arginine, histidine), acidic side chains (e.g., aspartic acid, glutamic acid), non-charged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), β-branched side chains (e.g., threonine, valine, isoleucine), and aromatic side chains (e.g., tyrosine, phenylalanine, tryptophan, histidine). Preferably, CDR3 regions in the VL and/or VH domains include no more than five conservative amino acid substitutions, more often no more than three conservative substitutions. Typically, conservative substitutions are not made at amino acid positions that are critical for binding the epitope of the TRBV9 family beta-chain.

The above variants (mutants) of antibodies according to the invention can be obtained by peptide synthesis or using recombinant DNA techniques as described in the "Nucleic acids" section below.

In preferred embodiments, the antibody comprises the constant region of heavy chain, such as the constant region of human IgG1, IgG2, IgGS, IgG4, IgA, IgE, IgM, IgD. Preferably, the heavy chain constant region is a human IgG1 heavy chain constant region. Furthermore, an antibody may comprise either a light chain constant region or a light chain kappa constant region or a light chain lambda constant region. Preferably, an antibody comprises a light chain kappa constant region.

In preferred embodiments, an antibody heavy chain variable fragment is characterized by a degree of humanization of 87%. In preferred embodiments, an antibody light chain variable fragment is characterized by a degree of humanization of 85%.

Also provided are antigen-binding fragments of antibodies of the present invention. The term "antigen-binding fragment" of an antibody (or "functional fragment of an antibody" or "active fragment of an antibody"), as used herein, refers to one or more antibody fragments that retain the ability to specifically bind an antigen. It has been shown that the antigen-binding function of an antibody can be performed by fragments of a full-length antibody. Examples of binding fragments encompassed within the term "antigen-binding portion" of an antibody include (a) a Fab fragment, a monovalent fragment consisting of VL, VH, CL and CH1 domains; (b) a F(ab)2 fragment, a bivalent fragment comprising two Fab fragments linked by a disulfide bridge at the hinge region; (c) a Fd fragment consisting of VH and CH1 domains; (d) a Fv fragment consisting of VL and VH domains of a single arm of an antibody; (e) a dAb fragment (Ward et al. (1989) Nature 341:544-546) that consists of a VH domain, and (f) an isolated complementarity determining region (CDR). Furthermore, although the two domains of the Fv fragment, VL and VH, are encoded by separate genes, they can be linked, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; Huston et al. (1988) Proc. Natl. Acad. Sci. USA 85:5879-5883). Such single chain antibodies are also contemplated to be encompassed within the term "antigen-binding fragment" of an antibody. They also include other forms of single chain antibodies, such as diabodies. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger P. et al. (1993) Proc. Natl. Acad. Sci. USA 90:6444-6448; Poljak R. J. et al. (1994) Structure 2:1121-1123).

Antibody fragments, such as Fab and F(ab')2, may be obtained from whole antibodies using conventional techniques, such as papain or pepsin digestion, respectively, of whole antibodies. Moreover, antibodies, antibody fragments and immunoadhesion molecules can be obtained using standard recombinant DNA techniques.

An antibody or antigen-binding portion thereof may be part of larger immunoadhesion molecules formed by covalent or noncovalent association of the antibody or antibody fragment with one or more protein or peptide. Examples of such immunoadhesion molecules include use of a streptavidin core region to make a tetrameric scFv molecule (Kipriyanov S. M. et al. (1995) Human Antibodies and Hybridomas 6:93-101) and use of a cysteine residue, a marker peptide and a C-terminal polyhistidine tag to make bivalent and reduced-size scFv biomolecules (Kipriyanov S. M. et al. (1994) Mol. Immunol., 31:1047-1058). Other chemical bonds between antibody fragments are also well known from the state of art.

Antibodies and functional fragments thereof according to the invention are present in an isolated form, i.e. this means that such a protein is substantially free from the presence of other proteins or other naturally occurring biological molecules, such as oligosaccharides, nucleic acids and fragments thereof, etc., wherein the term "substantially free" in this case means that less than 70%, typically less than 60%, and more often less than 50% of said composition comprising the isolated protein is other naturally occurring biological molecule. In some embodiments, said proteins are present in substantially purified form, wherein the term "substantially purified form" means a purity equal to at least 95%, typically equal to at least 97%, and more often equal to at least 99%.

Methods for purifying an antibody obtained by recombinant or hybridoma techniques are well known in the art, for example, purification can be performed by chromatography (for example, ion exchange chromatography, affinity chromatography, especially affinity for the specific antigens Protein A or Protein G, and sizing column chromatography), centrifugation, differential solubility, or any other standard technique for purifying proteins. Furthermore, antibodies obtained by the technology according to the present invention or fragments thereof can be fused to heterologous polypeptide sequences (e.g., a histidine tag) to facilitate purification. Antibody affinity can be determined using the standard analysis by determining dissociation constants (KD). KD is calculated using the equation KD=kdis/kon, where kdis is the experimentally calculated dissociation rate constant and kon is the experimentally calculated association rate constant of the antibody-antigen complex.

Preferred antibodies are those that bind a human antigen with a KD value of not more than about $1\times10^{-7}$ M; preferably not more than about $1\times10^{-8}$ M; more often not more than about $1\times10^{-9}$ M; more preferably not more than about $1\times10^{-10}$ M, and most preferably not more than about $1\times10^{-11}$ M, for example, not more than about $1\times10^{-12}$ M.

Preferred antibodies include the antibody MA-042 described in detail in the experimental section below.

Antibodies and fragments thereof that can be used in the present compositions and methods are biologically active antibodies and fragments, i.e. they are capable of binding the desired antigenic epitopes and exhibiting the biological effect directly or indirectly.

Antibodies and functional fragments thereof according to the invention are able to specifically bind the epitope (region) of the TRBV9 family beta-chain. In preferred embodiments, as a result of their specific binding to the beta chain of the TRBV9 family, inhibition of the activity of TCRs that include said beta-chain. Typically, inhibition amounts to preferably at least about 20, or 30, or 40, or 50, or 60, or 70, or 80, or 90, or 95% or higher.

In some embodiments, an antibody against the TRBV9 family beta-chain according to the invention or a fragment thereof can eliminate T cells bearing TCR comprising the TRBV9 family beta-chain. In some embodiments, an antibody or fragment thereof according to the invention can provide at least about 20%, at least about 30%, at least about 40%, at least about 50%, at least about 60%, at least about 70%, at least about 80%, at least about 90%, at least about 95%, or about 100% elimination of T lymphocytes.

In a preferred embodiment of the invention, the antibody is antibody MA-042.

The antibody MA-042 includes the variable domains of heavy and light chains, which have the amino acid sequences shown in SEQ ID NOs: 16 and 18.

The antibody MA-042 includes heavy and light chains, which have the amino acid sequences shown in SEQ ID NOs: 20 and 22, respectively.

Nucleic Acids

The present invention provides nucleic acid molecules encoding the heavy and light chains of an antibody of the present invention, functional fragments and variable domains thereof, which can be used to obtain chimeric antibodies including the variable domains of the invention operatively fused with the known constant domains of human antibodies.

In preferred embodiments, a nucleic acid of the invention encodes an antibody heavy chain, the variable domain of which contains 3 hypervariable regions, HCDR1, HCDR2 and HCDR3, wherein HCDR1 (according to the Kabat numbering scheme) has the amino acid sequence of SEQ ID No 1;
HCDR2 has the amino acid sequence of SEQ ID No 2;
HCDR3 has the amino acid sequence of SEQ ID No 3.

In preferred embodiments, a nucleic acid of the invention encodes an antibody light chain, the variable domain of which comprises 3 hypervariable regions, LCDR1, LCDR2 and LCDR3, wherein:

LCDR1 has the amino acid sequence of SEQ ID No 4;
LCDR2 has the amino acid sequence of SEQ ID No 5;
LCDR3 has the amino acid sequence of SEQ ID No 6.

In preferred embodiments, a nucleic acid of the invention encodes antibody heavy and light chain variable domains, which contain amino acid substitutions in the FR fragments of variable domains of heavy and light chain, which increase the degree of humanization of the antibody as compared to the parental one.

Nucleic acid molecules encoding the homologs and mutants of said antibody chains, functional fragments and domains thereof are also within the scope of the present invention.

In some embodiments, a nucleic acid encodes the variable domain of heavy chain of an antibody of the present invention, which contains at least 10 humanizing amino acid substitutions as compared to the variable domain of heavy chain of the parental antibody, the amino acid sequence of which is shown in SEQ ID No 8.

In some embodiments, a nucleic acid encodes an antibody heavy chain, the variable domain of which has the amino acid sequence of SEQ ID No: 16.

In some embodiments, a nucleic acid encodes an antibody light chain, the variable domain of which comprises at least 10 humanizing amino acid substitutions as compared to the variable domain of light chain of the parental antibody, the amino acid sequence of which is shown in SEQ ID No 10.

In some embodiments, a nucleic acid encodes an antibody light chain, the variable domain of which has the amino acid sequence of SEQ ID No: 18.

In some embodiments, a nucleic acid encodes an antibody heavy chain, the amino acid sequence of which is at least 85% identical, or at least 90% identical, or at least 91% identical, or at least 92%, or at least 93% identical, or at least 94%, or at least 95%, or at least 96%, or at least 97%, or at least 98% or at least 99% or 100% identical to the amino acid sequence of SEQ ID NO: 20.

In some embodiments, a nucleic acid encodes an antibody light chain, the amino acid sequence of which is at least 85% identical, or at least 90% identical, or at least 91% identical, or at least 92%, or at least 93% identical, or at least 94%, or at least 95%, or at least 96%, or at least 97%, or at least 98% or at least 99% or 100% identical to the amino acid sequence of SEQ ID NO: 22.

Examples of nucleic acids encoding light and heavy chains of the invention are shown in SEQ ID Nos: 19 and 21.

Nucleic acids encoding the variable domains of light and heavy chain of antibody are also of interest. Nucleic acids encoding the variable domains of light and heavy chain of antibody can be used for operable fusion with nucleic acids encoding the corresponding constant domains of the antibodies.

In some embodiments, a nucleic acid encodes the variable domain of heavy chain of antibody, the amino acid sequence of which is shown in SEQ ID No: 16.

In some embodiments, a nucleic acid encodes the variable domain of light chain of antibody, the amino acid sequence of which is shown in SEQ ID No: 18.

Examples of nucleic acids encoding the variable domains of heavy and light chain of antibody are shown in SEQ ID Nos: 15 and 17.

As used herein, a "nucleic acid molecule" or "nucleic acid" is a DNA molecule, such as a genomic DNA molecule or a cDNA molecule, or an RNA molecule, such as an mRNA molecule. In some embodiments, a nucleic acid molecule of the present invention is a DNA (or cDNA) molecule containing an open reading frame that encodes an antibody or antibody fragment of the present invention and is capable, under suitable conditions (e.g., physiological intracellular conditions), of being used for expression in a heterologous expression system.

In some embodiments, a nucleic acid molecule of the present invention is produced by genetic engineering methods. Methods for producing nucleic acids are well known in the art. For example, the availability of amino acid sequence information or nucleotide sequence information enables preparation of isolated nucleic acid molecules of the present invention by oligonucleotide synthesis. In the case of amino acid sequence information, a number of nucleic acids that differ from each other due to degenerate code may be synthesized. The methods to select codon variants for a desired host are well known in the art.

Synthetic oligonucleotides may be prepared by the phosphoramidite method, and the resultant constructs may be purified according to methods well-known in the art, such as high performance liquid chromatography (HPLC) or other methods as described in, for example, Sambrook et al., Molecular Cloning: A Laboratory Manual, 2nd Ed., (1989) Cold Spring Harbor Press, Cold Spring Harbor, N.Y., and under the instruction described in, e.g., United States Dept. of HHS, National Institute of Health (NIH) Guidelines for Recombinant DNA Research. Long, double-stranded DNA molecules of the present invention may be synthesized in the following manner: by synthesizing several smaller fragments of appropriate complementarity that comprise appropriate termini capable of cohesion with an adjacent fragment. Adjacent fragments may be linked using DNA ligase or PCR-based method.

The nucleic acid molecules of the present invention may be also cloned from biological sources.

The present invention also encompasses nucleic acids that are homologous, substantially the same as, identical to, or derived from nucleic acids encoding polypeptides of the present invention.

Nucleic acids of the invention are present in an environment other than that in which they are present in nature, for example, they are isolated, present in an increased amount, present or expressed in in vitro systems or in cells or organisms other than those in which they are present in nature.

Changes or differences in nucleotide sequence between closely related nucleic acid sequences may represent nucleotide changes in the sequence that arise during the course of normal replication or duplication. Other changes may be specifically designed and introduced into the sequence for specific purposes, such as to change the codons of specific amino acids or a nucleotide sequence in a regulatory region. Such specific changes may be made in vitro using a variety of mutagenesis techniques or produced in host organisms placed under specific selection conditions that induce or select for these changes. Such specifically obtained sequence variants can be called "mutants" or "derivatives" of the original sequence.

Mutant or derivative nucleic acids can be obtained on a template nucleic acid selected from the above nucleic acids by modification, deletion or addition of one or more nucleotides in the template sequence, or a combination thereof, to obtain a variant of the template nucleic acid. The modifications, additions or deletions can be performed by any method known in the art (see, e.g., Gustin et al., Biotechniques (1993) 14: 22; Barany, Gene (1985) 37: 111-123; and Colicelli et al., Mol. Gen. Genet. (1985) 199:537-539, Sambrook et al., Molecular Cloning: A Laboratory Manual, (1989), CSH Press, pp. 15.3-15.108) including error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, random mutagenesis, gene reassembly, gene site saturated mutagenesis (GSSM), synthetic ligation reassembly (SLR), or a combination thereof. The modifications, additions or deletions may also be performed by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and a combination thereof.

Also provided are degenerate variants of nucleic acids that encode the proteins of the present invention. The degenerate variants of nucleic acids include replacements of the codons of nucleic acid with other codons encoding the same amino acids. In particular, the degenerate variants of nucleic acids are created to increase the expression in a host cell. In this embodiment, the codons of nucleic acid that are non-preferred or less preferred in genes in the host cell are replaced with the codons over-represented in coding sequences in genes in the host cell, wherein said replaced codons encode the same amino acid.

The above modifications do not substantially alter the properties of antibodies or functional fragments thereof, but can facilitate protein folding in a host cell, decrease aggregation capacity or modulate other biochemical properties of the proteins, for example, half-life period. In some embodiments, these modifications do not modify biochemical properties of the protein. In some embodiments, these modifications lead to reduced antibody immunogenicity. All types of modifications and mutations specified above are performed at the nucleic acid level.

The disclosed nucleic acids may be isolated and prepared in a substantially purified form. A substantially purified form means that the nucleic acids are at least about 50% pure, typically at least about 90% pure and typically are "recombinant", i.e. flanked by one or more nucleotides with which it is not typically associated on a chromosome that occurs in nature in the natural host organism thereof.

Also provided are nucleic acids that encode fusion proteins comprising a protein of the present invention, or fragments thereof, which are discussed in more detail below. Nucleic acids encoding variable domains of the invention can be operatively linked to nucleic acids encoding the corresponding constant domains of the light and heavy chains of an antibody. Nucleic acids encoding the light and heavy chains of an antibody can be operatively linked to nucleic acids encoding a leader peptide that facilitates the transport of expression products from the host cell. The leader peptide is subsequently removed during maturation of the polypeptide.

Vector

Also provided are a vector and other nucleic acid constructs comprising the disclosed nucleic acids. The term "vector" refers to a nucleic acid molecule capable of transporting another nucleic acid to which it has been operatively linked. Certain vectors can autonomously replicate in host cells to which they were introduced, while other vectors can integrate into host cell genome and replicate together with the host genome. Moreover, some vectors are capable of directing the expression of genes to which they have been operatively linked. Such vectors are called herein "recombinant expression vectors" (or simply "expression vectors") and illustrative vectors are well known from the prior art. Suitable vectors include viral and non-viral vectors, plasmids, cosmids, phages, etc., preferably plasmids, and are used for cloning, amplifying, expressing, transferring, etc. of a nucleic acid sequence of the present invention to an appropriate host. The choice of appropriate vector is obvious to those skilled in the art. A full-length nucleic acid or a portion thereof is inserted into a vector typically by means of DNA ligase attachment to a cleaved restriction enzyme site in the vector. Alternatively, the desired nucleotide sequence can be inserted by homologous recombination in vivo, typically by attaching regions of homology to the vector on the flanks of the desired nucleotide sequence. Regions of homology are added by ligation of oligonucleotides, or by polymerase chain reaction using primers comprising, for example, both the region of homology and a portion of the desired nucleotide sequence. Typically, a vector has an origin of replication ensuring propagation thereof in host cells as a result of introduction thereof into a cell as an extrachromosomal element. A vector may also comprise regulatory elements ensuring expression of a nucleic acid in the host cell and generation of the target polypeptide. In the expression vector, said nucleic acid is operatively linked to a regulatory sequence that may include promoters, enhancers, terminators, operators, repressors and inducers, as well as a start codon of the polypeptide. In some embodiments, a nucleic acid of the invention is further operatively linked to a leader peptide ensuring the isolation of an expression product from the host cell into the extracellular space.

Also provided are expression cassettes or systems used inter alia for the obtaining of the disclosed polypeptides (for example, the light and heavy chains of an antibody of the invention or variable domains of the light and heavy chains of an antibody of the invention) based thereon or for replication of the disclosed nucleic acid molecules. The expression cassette may exist as an extrachromosomal element or may be integrated into the cell genome as a result of introduction of said expression cassette into the cell. For expression, a protein product encoded by the nucleic acid of the invention is expressed in any convenient expression system, including, for example, bacterial systems, yeast, insects, amphibians, or mammalian cells. In the expression cassette, a target nucleic acid is operatively linked to regulatory sequences that can include promoters, enhancers, terminating sequences, operators, repressors and inducers, as well as a start codon of the polypeptide. In some embodiments, a nucleic acid of the invention is further operatively linked to a leader peptide ensuring the isolation of an expression product from the host cell into the extracellular space. Methods of obtaining expression cassettes or systems capable of expressing the desired product are known to those skilled in the art.

Host Cell

The above expression systems may be used in prokaryotic or eukaryotic hosts. Host-cells, such as *E. coli, B. subtilis, S. cerevisiae*, insect cells in combination with baculovirus vectors, or cells of a higher organism, which are not human embryonic cells, such as yeast, plants, vertebrates, e.g., CHO cells (e.g. ATCC CRL-9096), NS0 cells, SP2/0 cells, HEK293 cells, COS cells (e.g. ATCC CRL-1650, CRL-1651) and HeLa (e.g. ATCC CCL-2), may be used for the obtaining of the protein.

To produce an antibody of the invention, the host cell is co-transformed with an expression vector comprising a nucleic acid encoding an antibody light chain and an expression vector comprising a nucleic acid encoding an antibody heavy chain. In some embodiments, a single expression vector is used, into which nucleic acids encoding both the light and heavy chains of an antibody are introduced.

For expression of light and heavy chains, the expression vector(s) encoding the heavy and light chains are transformed (co-transformed) into a host cell such that the light and heavy chains are expressed in the host cell and preferably are secreted into the medium, in which the host cells are cultured, and from which medium the antibodies can be isolated. Various interpretations of the term "transformation" are intended to include a wide range of methods commonly used for introducing exogenous DNA into a prokaryotic or eukaryotic host cell, for example, electroporation, calcium phosphate precipitation, DEAE-dextran transfection, etc., as described in Sambrook, Fritsch and Maniatis (eds) Molecular Cloning; A Laboratory Manual, Second Edition, Cold Spring Harbor, N.Y. (1989; Ausubel F. M. et al. (eds.) Current Protocols in Molecular Biology, Green Publishing Associates (1989).

When recombinant expression vectors containing the nucleic acids of the antibody are introduced into host cells, the antibodies are obtained by culturing the host cells for a period of time sufficient to express the antibody in the host cell, or (more preferably) secrete the antibody into the culture medium, in which the host cells are grown. Antibodies can be isolated from a culture medium using standard protein purification techniques. Cell culture conditions are well known to those skilled in the art and described in Current Protocols in Cell Biology, Bonifacino J. S., Dasso M., Harford J. B., Lippincott-Schwartz J. and Yamada K. M. (eds.) published by John Wiley & Sons, Inc., 2000.

If any of the above host cells or other host cells or organisms suitable for replication and/or expression of the nucleic acids of the invention are used, the resulting replicated nucleic acid, expressed protein or polypeptide are within the scope of the invention as a product of the host cell or organism. The product may be isolated by a suitable technique known in the art.

The cell lines, which stably express the proteins of present invention, can be selected by the methods known in the art (e.g. co-transfection with a selectable marker, such as dhfr, gpt, neomycin, hygromycin, which allows the identification and isolation of the transfected cells that contain the gene integrated into a genome).

The nucleic acid molecules of the present invention may also be used to determine gene expression in a biological sample. A method in which cells are examined for the presence of specific nucleotide sequences, such as genomic DNA or RNA, is well established in the art. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable carrier, e.g. nitrocellulose, nylon, etc., and then probed with a fragment of the subject DNA as a probe. Other techniques, such as oligonucleotide ligation assays, in situ hybridizations, and hybridization to DNA probes immobilized on a solid chip may also find use. Detection of mRNA hybridizing to the subject sequence is indicative of gene expression in the sample.

Therapeutic Use of Antibodies of the Invention

In one aspect, an antibody or active fragment thereof of the present invention is used in the treatment of disorders that are associated with the activity of pathological T lymphocytes bearing the surface TRBV9 family TCRs, for example, exhibiting activity of autoimmune T lymphocytes in AS, celiac disease, T cell lymphomas.

The term "patient", as used in this application, refers to a mammal including but not limited to mice, monkeys, humans, livestock mammals, sports mammals and pet mammals; preferably the term applies to humans. In a particular embodiment, the patient is further characterized by a disease or disorder, or condition, mediated by the presence in the body thereof of TCR, the beta-chain of which belongs to the TRBV9 family. As is known from the prior art, TCR, the beta-chain of which belongs to the TRBV9 family, is associated with AS and celiac disease. Furthermore, TCR, the beta-chain of which belongs to the TRBV9 family, may be associated with the development of a number of blood diseases, such as T cell lymphoma caused by the Epstein-Barr virus.

As used herein, the terms "co-administration", "co-administered" and "in combination with" referring to the antibody with one or more other therapeutic agents, are contemplated to mean, refer to and include the following:

1) simultaneous administration of such combination of an antibody of the invention and a therapeutic agent to a patient in need of treatment, when such components are formulated together into a single dosage form which releases said components at substantially the same time to said patient,
2) simultaneous administration of such combination of an antibody of the invention and a therapeutic agent to a patient in need of treatment, when such components are formulated apart from each other into separate dosage forms which are taken at substantially the same time by said patient, whereupon said components are released at substantially the same time to said patient,
3) sequential administration of such combination of an antibody of the invention and a therapeutic agent to a patient in need of treatment, when such components are formulated apart from each other into separate dosage forms which are taken at consecutive times by said patient with a significant time interval between each administration, whereupon said components are released at substantially different times to said patient; and also
4) sequential administration of such combination of an antibody of the invention and a therapeutic agent to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

An antibody of the invention can be administered without further therapeutic treatment, i.e. as an independent therapy. Furthermore, treatment by an antibody of the invention may comprise at least one additional therapeutic treatment (combination therapy). In some embodiments of the invention, an antibody can be co-administered or formulated with another medicament/drug for an autoimmune or oncological disease, the pathogenesis of which involves TCRs comprising the TRBV9 beta-chain, for example, AC, celiac disease, T cell lymphoma, T cell leukemia.

Doses and Routes of Administration

An antibody of the invention will be administered in an amount that is effective in treatment of the condition in question, i.e. in doses and during the periods of time required to achieve the desired result. A therapeutically effective amount may vary according to factors such as the specific condition to be treated, age, sex, and weight of a patient, and whether the antibody is administered alone or in combination with one or more additional immunosuppressive or anti-inflammatory treatment techniques.

Dosage regimens may be adjusted to provide the optimum response. For example, a single bolus may be administered, several divided doses may be administered over time or the dose may be proportionally reduced or increased as indicated by the exigencies of the therapeutic situation. It is especially advantageous to formulate parenteral compositions in a unit dosage form for ease of administration and uniformity of dosage. A standard dosage form as used herein is intended to refer to physically discrete units suited as unitary dosages for patients/subjects to be treated; each unit contains a predetermined quantity of active compound calculated to produce the desired therapeutic effect in association with the desired pharmaceutical carrier. Specification for the standard dosage forms of the invention is typically dictated by and directly dependent on (a) the unique characteristics of a chemotherapeutic agent and particular therapeutic or prophylactic effect to be achieved, and (b) the limitations inherent in the art of compounding such an active compound for the treatment of sensitivity in the subjects.

Thus, a skilled artisan would appreciate, based upon the disclosure provided herein, that the doses and dosage regimen are adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Thus, although some doses and regimen schemes are given as examples in this document, these examples in no way limit the doses and regimens of administration that may be necessary for the patient in the practice of the present invention.

It is to be noted that dosage values may vary with the type and severity of the condition to be alleviated, and may include single or multiple doses. Furthermore, it is to be understood that for any particular subject, specific dosage regimens should be adjusted over time according to the individual need and the judgment of a medical professional administering or supervising the administration of the compositions, and that dosage ranges set forth herein are exemplary only and are not intended to limit the scope or practice of the claimed compositions. Furthermore, the dosage regimen with the compositions of the present invention can be based on various factors, including the type of a disease, age, weight, gender, patient's health condition, severity of a condition, route of administration and a particular antibody used. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the person skilled in the art. Methods for determining appropriate dosages and regimens are well-known in the art and would be understood by a skilled artisan once provided the ideas disclosed herein.

Examples of suitable administration methods are provided above.

It is contemplated that a suitable dose of an antibody of the invention will be in the range of 0.1-200 mg/kg, preferably 0.1-100 mg/kg, including about 0.5-50 mg/kg, for example about 1-20 mg/kg. An antibody may be administered, e.g. in a dose of at least 0.25 mg/kg, such as at least 0.5 mg/kg, including at least 1 mg/kg, e.g. at least 1.5 mg/kg, such as at least 2 mg/kg, e.g. at least 3 mg/kg, including at least 4 mg/kg, e.g. at least 5 mg/kg; and for example up to a maximum of 50 mg/kg, including up to a maximum of 30 mg/kg, e.g. up to a maximum of 20 mg/kg, including up to a maximum of 15 mg/kg. The administration will typically be repeated in appropriate time intervals, such as once a week, once every two weeks, once every three weeks or once every four weeks, and for as long as deemed appropriate by a responsible physician, who may, in some cases, increase or reduce the dose if necessary.

Pharmaceutical Composition

An antibody of the invention can be incorporated into a pharmaceutical composition suitable for administration to a patient. The antibodies of the invention may be administered alone or in combination with a pharmaceutically acceptable carrier, diluent, and/or excipients, in single or multiple doses. Pharmaceutical compositions for administration are designed to be appropriate for the selected mode of administration, and pharmaceutically acceptable diluents, carriers, and/or excipients, such as dispersing agents, buffers, surfactants, preservatives, solubilizing agents, isotonicity agents, stabilizing agents and the like be used as appropriate. Said compositions are designed in accordance with conventional techniques as in e.g., Remington, The Science and Practice of Pharmacy, 19th Edition, Gennaro, Ed., Mack Publishing Co., Easton, Pa. 1995, which provides various techniques for obtaining the compositions as are generally known to practitioners.

"Medicament (drug)"—is a compound or a mixture of compounds as a pharmaceutical composition in the form of tablets, capsules, powders, lyophilisates, injections, infusion, ointments and other ready forms intended for restoration, improvement or modification of physiological functions in humans and animals, and also for treatment and preventing of diseases, for diagnostics, anesthesia, contraception, cosmetology and others. Any method for administering peptides, proteins or antibodies accepted in the art may be suitably employed for an antibody of the invention.

The term "pharmaceutically acceptable" refers to one or more compatible liquid or solid components that are suitable for administration in a mammal, preferably a human.

The term "excipient" is used herein to describe any ingredient other than the above ingredients of the invention. These are substances of inorganic or organic nature which are used in the pharmaceutical manufacturing in order to give drug products the necessary physicochemical properties.

The term "buffer", "buffer composition", "buffering agent" refers to a solution, which is capable of resisting changes in pH by the action of its acid-base conjugate components, and which allows the antibody drug to resist changes in pH. Generally, the pharmaceutical composition preferably has a pH in the range from 4.0 to 8.0. Examples of buffers used include, but are not limited to, acetate, phosphate, citrate, histidine, succinate, etc. buffer solutions.

The terms "tonic agent", "osmolyte" or "osmotic agent", as used herein, refer to an excipient that can increase the osmotic pressure of a liquid antibody formulation. "Isotonic" drug is a drug that has an osmotic pressure equivalent to that of human blood. Isotonic drugs typically have an osmotic pressure from about 250 to 350 mOsm/kg. As isotonic agents can be used, but are not limited to, polyols, saccharides and sucrose, amino acids, metal salts, for example, sodium chloride, etc.

"Stabilizer" refers to an excipient or a mixture of two or more excipients that provide the physical and/or chemical stability of the active agent. As stabilizers can be used amino acids, for example, but are not limited to, arginine, histidine, glycine, lysine, glutamine, proline; surfactants, for example, but are not limited to, polysorbate 20 (trade name: Tween 20), polysorbate 80 (trade name: Tween 80), polyethylene-polypropylene glycol and copolymers thereof (trade names: Poloxamer, Pluronic, sodium dodecyl sulfate (SDS); antioxidants, for example, but are not limited to, methionine, acetylcysteine, ascorbic acid, monothioglycerol, sulfurous acid salts, etc.; chelating agents, for example, but are not limited to, ethylenediaminetetraacetic acid (EDTA), diethylenetriaminepentaacetic acid (DTPA), sodium citrate, etc.

A pharmaceutical composition is "stable" if the active agent retains physical stability and/or chemical stability and/or biological activity thereof during the specified shelf life at storage temperature, for example, of 2-8° C. Preferably, the active agent retains both physical and chemical stability, as well as biological activity. The storage period is selected based on the results of stability test in accelerated or natural aging conditions.

A composition containing a monoclonal antibody of the invention may be administered to a patient exhibiting pathologies as described in this application using standard administration techniques, including peroral, intravenous, intraperitoneal, subcutaneous, pulmonary, transdermal, intramuscular, intranasal, buccal, sublingual, or suppository administration.

A pharmaceutical composition of the invention preferably contains or is a "therapeutically effective amount" of an antibody of the invention. The term "therapeutically effective amount" is intended to refer to an amount that is effective at dosages and for periods of time necessary to achieve the desired therapeutic result. A therapeutically effective amount of an antibody may vary according to factors such as disease state, age, sex, and weight of a subject, and the ability of an antibody or part thereof to elicit a desired response in a subject. A therapeutically effective amount is also one in which any toxic or detrimental effects are outweighed by the therapeutically beneficial effects of the antibody. "Prophylactically effective amount" is intended to refer to the amount that is effective at dosages and for periods of time necessary to achieve the desired prophylactic result. Since a prophylactic dose is prescribed for individuals before or at an early stage of disease, typically a prophylactically effective amount may be less than a therapeutically effective amount.

A therapeutically effective or prophylactically effective amount is at least a minimal therapeutically beneficial dose that is less than the toxic dose of an active agent. On the other hand, a therapeutically effective amount of an antibody of the invention is an amount that reduces, in mammals, preferably humans, the biological activity of autoimmune clones, for example, through binding TCR, the beta-chain of which belongs to the TRBV9 family, where the presence of said clones causes or contributes to undesirable pathological effects, or decreasing TCR, the beta-chain of which belongs to the TRBV9 family, causes a beneficial therapeutic effect in a mammal, preferably a human.

The route of administration of an antibody of the invention can be oral, parenteral, inhalation or local. Preferably, antibodies of the invention can be included in a pharmaceutical composition acceptable for parenteral administration. The term "parenteral" as used in this application includes intravenous, intramuscular, subcutaneous, rectal, vaginal or intraperitoneal administration. Intravenous, intraperitoneal or subcutaneous injections are preferred routes of administration. Acceptable pharmaceutical carriers for such injections are well known from the prior art.

As described in appropriate guidelines, pharmaceutical compositions should be sterile and stable under the conditions of production and storage in a container, which is provided by, for example, hermetically sealed vials (ampoules) or syringes. Thus, pharmaceutical compositions can be subjected to filtration sterilization after preparing the composition, or can be made microbiologically suitable by any other technique. A typical composition for an intravenous infusion can include 250-1000 ml of fluid such as sterile Ringer's solution, physiologic saline, dextrose solution or Hank's salt solution, and a therapeutically effective dose (for example, 1-100 mg/ml or more) of an antibody concentrate. Doses may vary depending on disease type and severity. It is well known from the state of medical art that doses for any of patients depend on multiple factors including patient's sizes, body surface area, age, specific compound to be administered, gender, duration and route of administration, general health state and other simultaneously administered medications. A typical dose can be, for example, in a range of 0.001-1000 µg; however, doses lower and higher than this illustrative range are anticipated, especially given the above mentioned parameters. The daily parenteral dosing regimen may be from 0.1 µg/kg to 100 µg/kg of overall body weight, preferably from 0.3 µg/kg to 10 µg/kg, and more preferably from 1 µg/kg to 1 µg/kg, even more preferably from 0.5 to 10 µg/kg of body weight per day. The treatment process can be monitored by periodical assessment of patient's health state. For repeated administration for several days or longer, depending on patient's condition, the treatment is repeated until the desired response or suppression of symptoms of a disease. However, another dosing regimens not described herein can also be applied. The desired dose may be administered by single bolus or multiple bolus dosing, or by means of a continuous infusion of an antibody depending on a pharmacokinetic breakdown desired by a practitioner.

These estimated amounts of an antibody are largely depending on a physician's decision. The intended effect is the key factor for choosing a proper dose and regimen. Factors considered herein include a certain disease to be treated, a certain mammal to receive the treatment, clinical condition of a certain patient, disorder cause, antibody administration site, specific antibody type, route of administration, administration regimen and other factors well known in the medical arts.

Therapeutic agents of the invention can be frozen or lyophilized and reconstituted in an appropriate sterile carrier prior to administration. Freeze-drying and reconstitution can result in some loss of antibody's activity. Doses can be adjusted to compensate this loss. In general, pharmaceutical composition pH values from 6 to 8 are preferable.

Article of Manufacture (Products) and Kits

A further embodiment of the invention is an article of manufacture that contains products used to treat autoimmune diseases and related conditions and malignant blood diseases, the pathogenesis of which involves TCRs bearing the TRBV9 family beta-chain. Such diseases include, for example, AS, celiac disease, T cell leukemia, T cell lymphoma and others.

The article of manufacture is a container with a label and package insert, which can be in a blister and/or package. Suitable containers include, e.g., vials, ampoules, syringes, etc. The containers may be made of various materials such as glass or polymer material. The container comprises a composition which is effective for treating a certain condition, and can have a sterile access port. At least one active ingredient in the composition is an antibody according to the invention. The label and package insert indicates that the drug is intended to be used to treat a certain condition. The label and/or package insert additionally contain instructions for administering the antibody composition in a patient, including indications, frequency, dose, route of administration, contraindications and/or precautions for such therapeutic products. In one embodiment, the package insert indicates that the composition is intended to be used for treating.

Furthermore, an article of manufacture may comprise, without limitation, other products necessary for commercial purposes or necessary for a consumer, such as solvents, diluents, filters, needles and syringes.

The invention also relates to kits that can be used for various purposes, for example, for assessment of the ability to kill T cells bearing the TRBV9 family TCRs, for purification or immunoprecipitation of the TRBV9 receptor from cells. For isolation and purification, the kit may contain an antibody coupled to beads (e.g., sepharose beads). The kit comprises a container, a label and a package insert.

Diagnostic Use

Antibodies of the invention are also used in diagnostic purposes (e.g., in vitro, ex vivo). For example, an antibody can be used for detecting or measuring the level of T lymphocytes comprising TRBV9 family TCRs in samples obtained from a patient (e.g., tissue sample or a sample of body fluid, such as an inflammatory exudate, blood, intestinal fluid, saliva or urine). Suitable methods for detection and measurement include immunoassays, such as flow cytometry, enzyme-linked immunosorbent assay (ELISA), chemiluminescent assay, radioimmunoassay, and immunohistology. The invention further includes kits, for example, diagnostic kits comprising antibodies described herein.

In order that this invention may be better understood, the following examples are set forth. These examples are for purposes of illustration only and are not to be construed as limiting the scope of the invention in any manner.

All publications, patents and patent applications referred to in this specification are incorporated herein by reference. Although the foregoing invention has been described in some detail by illustration and example in order to avoid ambiguous interpretation, the experts in this field based on the ideas disclosed in this invention will be quite clear that can be made certain changes and modifications without deviation from the essence and scope of the included embodiments of the invention.

Experimental Section

Example 1. In Silico Humanization of Antibody Variable Domain Sequences

As the parental (reference) sequences were used the sequences of variable domains of heavy and light chain of anti-TRBV9-2 antibody, the amino acid sequences of which are shown in SEQ ID Nos: 8 and 10.

The amino acid sequences of the variable domains of the heavy and light chains were compared with a pool of germline sequences of the variable domains of human immunoglobulins, germline sequences of variable domains of rat immunoglobulins, sequences of mature human and rat antibodies obtained from both open sources and donor library provided by Biocad (Russia). Ylab software package was used for the analysis (Biocad, Russia).

The analysis determined positions and combinations thereof that are most animal-like and not human-like in the sequences of variable domains of test antibodies. At the same time, amino acid combinations that are most often represented in human antibodies in these positions were determined. The artificial sequences of variable domains containing substitutions that increase the degree of humanization of the antibody were designed based on the resulting data.

Also, the nucleotide sequences encoding the subject amino acid variants were codon optimized to express the humanized antibody in CHO cell line. The humanized nucleotide sequences of variable domains of heavy and light chains (SEQ ID Nos: 15 and 17) were synthesized de novo and cloned into pEE-HC, pEE-CK vectors, IgG1 format (Xu et al. Front. Chem. Sci. Eng. 2015, 9(3): 376-380) at SalI/NheI and SalI/BsiWI restriction sites, respectively.

The nucleic acid sequences of the resulting light and heavy chains were validated by Senger sequencing. The antibody MA-042 was selected for further investigation, the amino acid and nucleotide sequences of light and heavy chains of which are shown in SEQ ID Nos: 19-22.

The antibody MA-042 includes the variable domains of heavy and light chains, which have the amino acid sequences shown in SEQ ID NOs: 16 and 18.

The degree of humanization of the variable domain of heavy chain of antibody MA-042 was 87%, whereas that of the variable domain of light chain was 85% (Table 1). The heavy chain constant domain is represented by the IgG1 format, Gm3 allotype.

TABLE 1

Comparison of degree of humanization between variable domains of parental antibody and antibody MA-042

| Antibody | Degree of humanization of heavy chain variable domain, % | Degree of humanization of light chain variable domain, % |
| --- | --- | --- |
| TRBV9-2 | 72 | 69 |
| MA-042 | 87 | 85 |

Example 2. Preparation of Recombinant Antibody and Determination of Affinity Thereof Vectors comprising nucleic acids encoding antibody MA-042 light and heavy chains, obtained as described in Example 1, were propagated in *E. coli* cells and purified using a plasmid DNA purification kit from Qiagen (Germany) and used to transfect CHO-Fut8 cell line using linear polyethyleneimine (PEI "MAX", "Polysciences", USA) according to the manufacturer's instructions. The resulting reaction mixtures were incubated at 37° C. on a shaker. 9 days after transfection, culture liquid was separated from cells by filtration through a 0.5/0.22 μm filter. After filtration, the culture liquid was used to isolate antibodies using affinity chromatography on 0.2 ml PreDictor RoboColumn MabSelect SuRe columns (GE Healthcare, USA) equilibrated with phosphate-buffered saline (PBS, pH 7.4). The column was then washed with 5 volumes of PBS. The carrier-bound protein was eluted using a 0.1 M glycine buffer pH 3. We collected the main peak containing protein and adjusted pH to neutral with 1 M Tris buffer (pH 7.5). All stages were conducted under 110 cm/h flow rate. The protein was then transferred to PBS (pH 7.4) using dialysis, filtered through a 0.22 μm filter, transferred to new sterile tubes.

Isolation quality was evaluated using 12% PAGE under denaturing conditions. Quantitative assessment was carried out by measuring NanoDrop2000 microspectrophotometer at 280A. The isolated protein was stored at −70° C.

Antibody affinity was determined on OctetRed 96 system (ForteBio, USA). Antigen at a concentration of 20 μg/ml was immobilized onto the surface of AR2G sensors (ForteBio) according to the standard protocol and manufacturer's instructions. Analysis was conducted at 30° C. using PBS comprising 0.1% Tween 20 and 0.1% BSA as a working buffer. After baseline recording, the sensors were immersed into wells containing antibody solution for 300 seconds, where the complex was associated. The complex dissociation in buffer solution was then detected for 600 seconds.

Binding curves, after subtracting a reference signal, were analyzed using Octet Data Analysis (Version 9.0) software in accordance with the standard procedure and using 1:1 Global interaction model. The resulting data (Table 2) showed that the antibody specifically and with high affinity binds to the human antigen.

TABLE 2

Antibody MA-042 affinity characteristics

| Antibody | KD (M) | kon(1/Ms) | kdis(1/s) | Full R^2 |
| --- | --- | --- | --- | --- |
| MA-042 | <1.0E−12 | 3.19E+05 | <1.0E−07 | 0.9758 |

Example 3. Preparation of Cell Line Stably Producing Antibody in IgG1 Format, and Production of Antibody The sequences of heavy and light chains of antibody MA-042 were prepared as described in Example 1 and cloned into pSX vectors at HindIII, XbaI restriction sites. The resulting plasmids were cultured in *E. coli* cells, and 600-700 μg was isolated using BenchPro (Life Technology, CIIIA) according to the manufacturer's instructions. Plasmids were linearized overnight using PvuI endonuclease, ethanol was then precipitated, the precipitate was dissolved in water, the concentration in the final volume was 900-1100 ng/μl.

The CHO-K1-S cell line was cultured in Ham's F12 Gibco medium (Thermo, USA). Transfection with gene constructs comprising encoding sequences of MA-042 chains was performed using electroporation on Nucleofector™ (Lonza, Switzerland) according to the manufacturer's protocol.

The day after transfection, the transfected cells were subject to antibiotic selection for 24 days by adding puromycin (final concentration of 7.2 μg/ml) and hygromycin B (final concentration of 640 μg/ml) to the medium. Antibiotic-resistant cell clones homogeneous in structure expressing high level of MA-042 were then selected.

For culturing CHO-K1-S expressing MA-042, a serum-free medium Ham's F12 Gibco (Thermo, USA) supplemented with 25-100 uM 2-deoxy-2-fluoro-L-fucose (Carbo-Synth, UK) was used. Monoclonal antibody MA-042 for preclinical studies was produced in 50 L HyClone single-use bioreactor fermenter (Thermo Fisher Scientific). Producer cells were removed from culture liquid using Millistak COHC depth filter (Merck-Millipore, USA). Primary purification of antibody from the cleared culture medium was performed on Protein A affinity sorbent. Target protein was specifically eluted with glycine buffer pH 3.3-3.8 under acidic conditions. The collected eluate was exposed to acidic pH for 30-60 min for the purpose of viral inactivation, and then neutralized with 1M Tris-HCl solution to pH 6.5-7.0.

Final chromatographic purification to remove possible impurities (DNA, producer cell proteins, released affine sorbent's ligand, aggregates and antibody fragments) was performed using CaptoAdhere sorbent (GE HealthCare LifeSciences) in a flow-through mode. Thus, the protein solution was flowed through prepared sorbent equilibrated with Tris buffer with pH 6.5-7.0, under low conductivity (<3 msec/cm$^2$). The purified protein was then subject to virus-removing filtration using Viresolve PRO filter kit (Millipore, USA), concentrating and diafiltration against the final buffer containing acetate buffer (pH 5.0-5.5) and trehalose.

Example 4. Use of Antibody for Specific Binding to TRBV9 Family TCR

The monoclonal antibodies MA-042 obtained as described in Example 3 were used to sort lymphocyte subpopulations. The antibodies were labeled with fluorescein using a fluorescein isothiocyanate reagent (Sigma, USA) according to the manufacturer's protocol. The number of fluorophores that reacted with antibody molecules was controlled by absorption spectrum ratio at wavelengths of 495/280 nm.

T lymphocytes were obtained from peripheral blood from a healthy donor. Blood was collected in EDTA Vacuette tubes (2×9 ml each), the mononuclear fraction was isolated according to the standard procedure described in (Kovalchuk L. V. et al. Immunology: Workshop-2010.-176 p.). After isolation, the cells were transferred to phosphate buffered saline (PBS) comprising 0.5% bovine serum albumin (BSA) and 2 mM EDTA. The total number of cells and viability thereof was determined by trypan blue staining method as described by Lang N. R. (Stimulation of lymphocytes M.: Medicine, 1976-288 p.). An equal volume of 0.1% trypan blue solution was added to the cell suspension, the stained (dead) and unstained blue cells were then counted in a Goryaev chamber. Based on these data, the percentage of dead cells in the test sample was determined.

To confirm the selectivity of binding of MA-042 to the target population of T-lymphocytes bearing membrane TCR belonging to the TRBV9 family, 500,000 cell aliquots of mononuclear fraction were added to PBS buffer comprising 0.5% bovine serum albumin (BSA), 2 mM EDTA pH8, antibodies MA-042 labeled with FITC, CD3-eFluor405 (T lymphocyte marker) (eBioscience, USA) and CD45-PC5 (eBioscience, USA) (total leukocyte marker) at a concentration of 100 ng/ml. 50 µl reaction mixtures were incubated at room temperature for 30 min, after which the cells were washed with PBS buffer supplemented with 0.5% BSA, 2 mM EDTA. After the staining procedure, the cells were used for sorting using flow cytometry (FACSARIA III, USA, FIG. 1). The use of these markers in staining made it possible to isolate the target-population cells, which bore surface TRBV9+, CD3+, CD45+, as well as to obtain negative-population cells, i.e. those corresponding to the immunophenotype "TRBV9-, CD3+, CD45+". The TRBV9+ and TRBV9- population cells from two replications were used for isolation of total RNA and sequencing of the TCR beta-chains. The resulting cell fractions were placed in RLT buffer (Quagen, Germany), RNA was isolated therefrom using Quiagen RNAeasy mini kit #217004 reagent kit (Quagen) according to the manufacturer's protocol. The cDNA was synthesized on isolated RNA template, fragments of T receptor beta-chain were amplified according to the protocol described in Britanova et al (J Immunol, 2016, 196(12) 5005-5013) using Mint cDNA synthesis kit (Eurogen, Russia). Illumina adapters (USA) were ligated to the produced amplicons, sequencing was performed on MiSeq Illumina platform according to the sequencer manufacturer's protocol. The sequencing data were analyzed using MiGEC, MiXCR and VDJtools software available on the Internet at: https://milaboratory.com. Analysis of resulting repertoires of TCR beta-chains showed that the libraries obtained by sorting using antibody MA-042 were enriched by 93% with sequences that were encoded by the TRBV9 gene segment, whereas no sequences comprising TRBV9 were detected in the repertoires of "TRBV9-" negative fraction beta-chains.

Example 5. In Vitro Functional Activity of Antibody MA-042

Figure 2A:
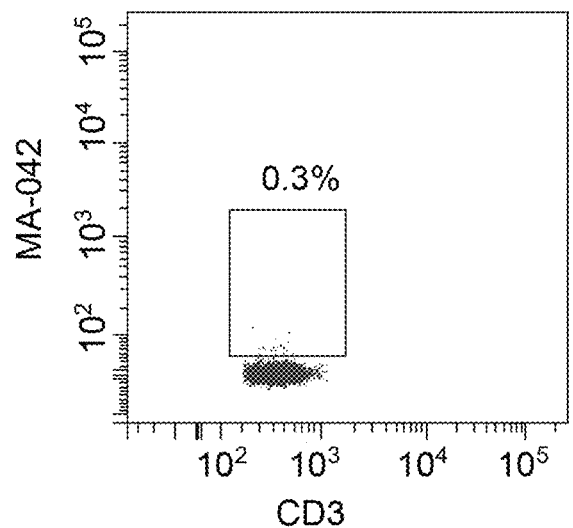
FIGS. 2A and 2B show the result of flow cytometry of T lymphocytes following a cytotoxic activity assay in the presence of antibody MA-042 at a concentration of 1 ng/ml (right) and 1 μg/ml (left). The rectangle shows the population of CD45+ CD3+TRBV9+.
Figure 2B:
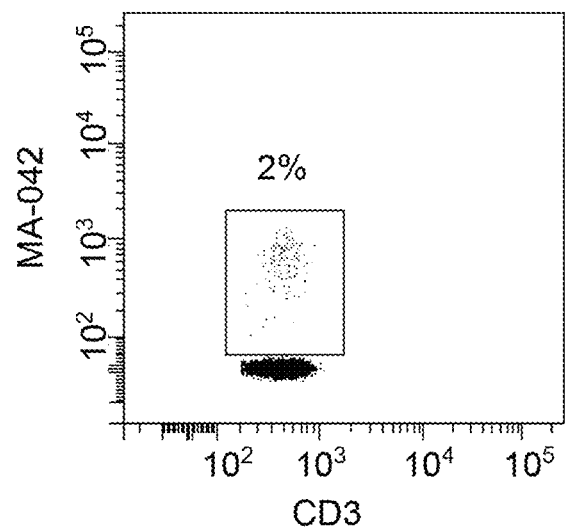
Figure 3:
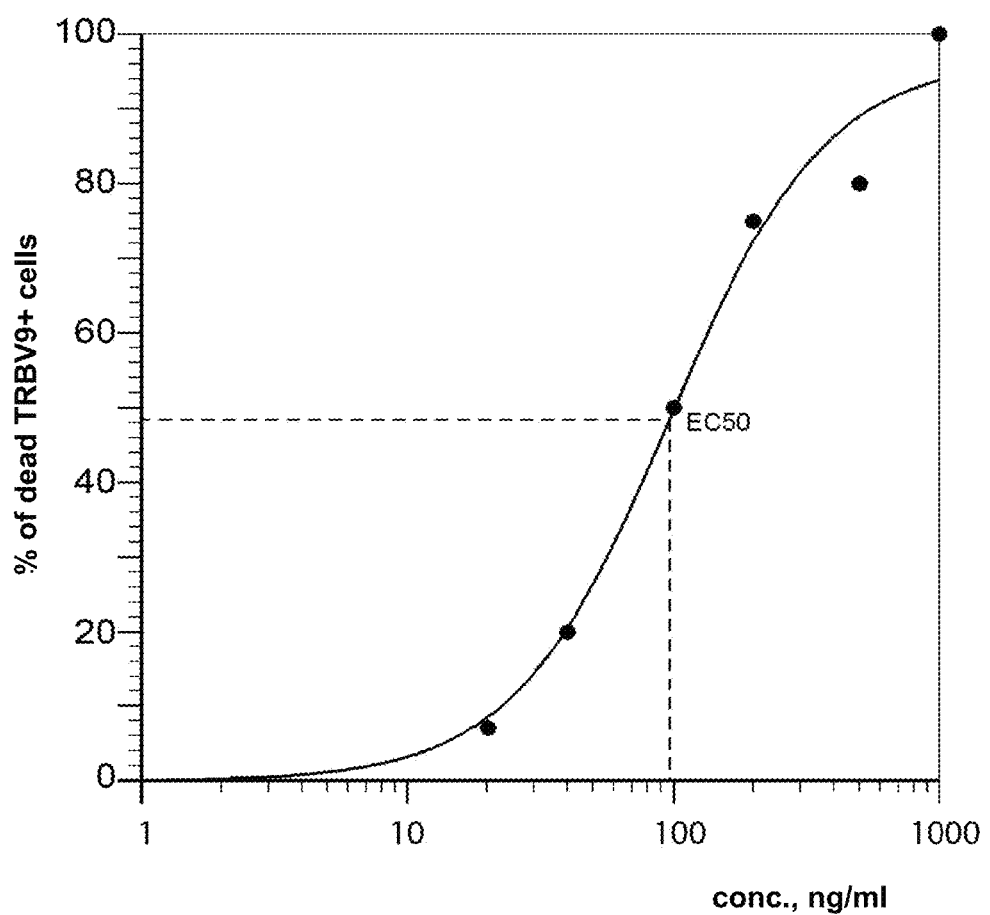
FIG. 3 shows a percentage of dead T lymphocytes as a function of MA-042 concentration to determine the half-effective concentration of MA-042 (EC50) in a cytotoxicity assay.

The monoclonal antibody MA-042 was obtained as described in Example 3. Mononuclear fraction of human blood was obtained as described in Example 4. Cytotoxic activity of MA-042 was determined using cytofluorometry method. A cell aliquot from the mononuclear fraction was used to calculate the total number of cells, viability was determined by the ability to stain with trypan blue. To assess cytotoxicity efficiency, 3-4×10$^6$ cells were incubated in PBS buffer for an hour with the antibody MA-042 at a concentration of: 20 ng/ml 40 ng/ml 100 ng/ml 200 ng/ml 500 ng/ml and 1 µg/ml, for "zero control", the cells were incubated without adding the antibody. After incubation, the cells were washed twice with PBS, transferred to RPMI medium comprising 10% human serum, and incubated for 72 hours in a $CO_2$ incubator. The cells were then centrifuged and stained with antibodies CD4-PE, CD3-eFluor405 (eBioscience, USA) and MA-042-FITC. Stained samples of cells were used in cytometric analysis on FacsAria III cell sorter (BD, USA). Cytotoxic effect was assessed by progressively decreasing proportion of TRBV9-positive cells in the CD3+ lymphocyte population, a decrease in the number of target cells correlated with an increase in antibody MA-042 concentration until complete elimination of the target population. Complete elimination of the target population following MA-042 staining was detected at antibody concentration of 500 ng/ml. In "zero control", the percentage of TRBV9 T lymphocytes remained unchanged. FIG. 2 shows a typical result of flow cytometry. EC50 value was thus obtained (half-maximal effective concentration refers to antibody concentration to induce half of a given antibody's maximum effect after a specified period of time), which amounted to 100 ng/ml for the antibody MA-042 (FIG. 3).

Example 6. In Vivo Functional Activity of Antibody MA-042

Monoclonal antibody MA-042 was obtained as described in Example 3. A single intravenous administration of MA-042 to rhesus macaques (*Macaca mulatta*) was performed to assess specific activity and basic pharmacokinetic parameters. The experiment was performed on sexually mature male rhesus macaques weighing 4-10 kg, which were provided by the Federal State Budget Scientific Institution "Scientific Research Institute of Medical Primatology". Following delivery, the animals were subject to 30-day quarantine.

Fractional content of TRBV9+ lymphocytes in peripheral blood was preliminary estimated to form a cohort of experimental and control animals. Animals' venous blood was collected into EDTA vacuum tubes (Vacuette, Greiner Bio-One, Austria) at 4 ml/tube. A mononuclear cell fraction (1.077 g/cm3 PanEco, Russia) was then isolated by Ficoll gradient. For immunophenotyping, we used 100,000 cells, which were supplemented with 1 µl of commercial anti-CD8 PE/Cy5 (clone RPA-T8) antibodies (BioLegend, USA), anti-CD4-Alexa Fluor 488 (clone S3.5) antibodies (Thermo Fisher, USA) and anti-CD2-PerCP Cy 5.5 (clone RPA-2.10) antibodies (BioLegend, USA), anti-TcRVβ1 (TRBV9)-PE antibodies (Beckman Coulter, USA), incubated at room temperature for 20 minutes and washed 2 times with an equal volume of Hanks' solution. The samples were analyzed using FACSAria III cell sorter (USA).

For the time of the experiment, the selected animals were kept in individual metal cages equipped with feed bins, label holders, at 1 animal per cage. The diet was made up of all-in-one feed, fruits, vegetables according to average feeding standards. The animals received water from a central water supply.

Based on the results of cytometric analysis with antibodies to main lymphocyte surface determinants (CD4, CD8, CD2), animals were divided into three groups at 4 animals/group, including the control group. The control group of animals intravenously received human immunoglobulin ("Immunovenin", Microgen, Russia).

Two experimental groups were administered with MA-042 at doses of 1 and 10 mg per animal, respectively, for a comparative study of the percentage (%) of TRBV9+ T cells in the peripheral blood of rhesus macaques (*Macaca mulatta*) as a function of product dose. "Immunovenin" was diluted with sterile water according to the instructions and administered at a concentration of 10 mg per animal. The MA-042 product was diluted with Dulbecco's phosphate-buffered saline (DPBS) without calcium and magnesium. The products were administered into the ulnar vein of right forelimb in a volume not exceeding 5 ml per injection.

The observation period lasted 42 days. Blood samples were selected as indicated in Table 3. Immunophenotyping and analysis of samples was performed as described above.

TABLE 3

Whole blood sampling scheme for determining percentage (%) of TRBV9+ among T cells.

| Week | Day | Hour | Remark |
|---|---|---|---|
| 1 | 1 | 0 | Background (prior to first administration) |
| 1 | 4 | 72 | 72 hours following administration |
| 1 | 7 | 144 | 144 hours following administration |
| 3 | 15 | 336 | 336 hours following administration |

TABLE 3-continued

Whole blood sampling scheme for determining percentage (%) of TRBV9+ among T cells.

| Week | Day | Hour | Remark |
|---|---|---|---|
| 4 | 25 | 576 | 576 hours following administration |
| 6 | 42 | 984 | 984 hours following administration |

As a result, 72 hours following administration of MA-042, the animals exhibited almost complete elimination of TRBV9+ in peripheral blood at the both concentrations. A portion of TRBV9+ lymphocytes was detected 336 hours following administration of the product at a concentration of 1 mg/animal No TRBV9+ lymphocytes were detected in animals that received the product at a dose of 10 mg. 42 days following administration, no cases of TRBV9+ lymphocytes were detected in the experimental groups; the control group exhibited the same level of TRBV9+ lymphocytes as it was before the experiment.

Example 8. Preparation of Pharmaceutical Composition Comprising Antibody of the Invention The pharmaceutical composition was obtained by standard techniques that are known in the art.

The pharmaceutical composition's components are shown in Table 4.

TABLE 4

Concentrations of pharmaceutical composition's components

| Component | Concentration |
|---|---|
| Antibody MA-042 | 10-50 mg/ml |
| 10 mM citrate buffer to pH | 6.0-7.0 |
| Sodium chloride | 50-150 mM |
| Sucrose, trehalose | 0.3-0.5% |
| Water for injections | up to 1 ml. |

Example 9. Kit Comprising Pharmaceutical Composition with Antibodies

To produce kits with a dosage form comprising an antibody MA-042 composition, the pharmaceutical composition prepared according to Example 5 is sealed in 1 ml ampoules or syringes under sterile conditions, labeled and packaged into plastic or cardboard containers.

Also, an insert is included in the ampoule container.

The invention claimed is:

1. A monoclonal antibody or antigen-binding fragment thereof that specifically binds to the TRBV-9 family beta-chain region of the human T cell receptor, comprising a heavy chain variable domain, the amino acid sequence of which is shown in SEQ ID No: 16 and a light chain variable domain, the amino acid sequence of which is shown in SEQ ID No: 18.

2. The monoclonal antibody according to claim 1, which includes a heavy chain having the amino acid sequence of SEQ ID No: 20 and a light chain having the amino acid sequence of SEQ ID No: 22.

3. The monoclonal antibody according to claim 2, which is a full-length IgG antibody.

4. A nucleic acid that encodes a monoclonal antibody or antigen-binding fragment thereof according to claim 1, wherein the antibody or antigen binding fragment thereof specifically binds to the TRBV9 family beta-chain region of the human T receptor.

5. An expression vector containing a nucleic acid according to claim 4.

6. A method of obtaining a host cell for producing an antibody or antigen-binding fragment thereof that specifically binds to the TRBV-9 family beta-chain region of the human T cell receptor, comprising a heavy chain variable domain, the amino acid sequence of which is shown in SEQ ID No: 16 and a light chain variable domain, the amino acid sequence of which is shown in SEQ ID No: 18 comprising co-transformation of a cell with a vector according to claim 5.

7. A host cell for obtaining an antibody or antigen-binding fragment thereof that specifically binds to the TRBV-9 family beta-chain region of the human T cell receptor, comprising a heavy chain variable domain, the amino acid sequence of which is shown in SEQ ID No: 16 and a light chain variable domain, the amino acid sequence of which is shown in SEQ ID No: 18 comprising a nucleic acid according to claim 4.

8. A method of obtaining an antibody or antigen-binding fragment thereof according to claim 1, comprising culturing a host cell for obtaining a monoclonal antibody or antigen-binding fragment thereof that specifically bind to the TRBV-9 family beta-chain region of the human T cell receptor, comprising a heavy chain variable domain, the amino acid sequence of which is shown in SEQ ID No: 16 and a light chain variable domain, the amino acid sequence of which is shown in SEQ ID No: 18 in a culture medium under conditions ensuring the production of said antibody, followed by isolation and purification of the obtained antibody.

9. A pharmaceutical composition comprising an antibody or antigen-binding fragment thereof according to claim 1 in combination with one or more pharmaceutically acceptable excipients.

10. The pharmaceutical composition according to claim 9, wherein the composition is for treating a disease or disorder mediated by the TRBV9 family beta-chain region of the human T receptor.

11. A pharmaceutical composition comprising an antibody or antigen-binding fragment thereof according to claim 1 and at least in a therapeutically effective amount one other therapeutically active compound.

12. The pharmaceutical composition of claim 10, wherein said disease or disorder is ankylosing spondylitis, celiac disease, T cell leukemia, or T cell lymphoma.

13. The pharmaceutical composition according to claim 11, wherein the composition is for treating a disease or disorder mediated by the human T cell receptor bearing the TRBV9 family beta-chain.

14. The pharmaceutical composition of claim 13, wherein said disease or disorder is ankylosing spondylitis, celiac disease, T cell leukemia, or T cell lymphoma.

15. The pharmaceutical composition according to claim 14, wherein the other therapeutically active compound is selected from a small molecule, antibody or steroid hormones.

16. A method for inhibiting the biological activity of the T cell receptor, the beta-chain of which belongs to the TRBV9 family, in a subject in need of such inhibition, comprising administering to the subject an effective amount of an antibody or antigen-binding fragment thereof according to claim 1.

17. A method for treating a disease or disorder mediated by the human T cell receptor bearing the TRBV9 family beta-chain, comprising administering to a subject in need of such treatment an antibody or antigen-binding fragment thereof according to claim 1 in a therapeutically effective amount.

18. The method for treating a disease or disorder according to claim 17, wherein the disease or disorder is selected from the group: ankylosing spondylitis, celiac disease, T cell leukemia, T cell lymphoma.

19. A method for treating a disease or disorder mediated by the human T cell receptor bearing the TRBV9 family beta-chain, comprising administering to a subject in need of such treatment a pharmaceutical composition according to claim 9 in a therapeutically effective amount.

20. The method for treating a disease or disorder according to claim 19, wherein the disease or disorder is ankylosing spondylitis, celiac disease, T cell leukemia, or T cell lymphoma.

21. A method for treating a disease or disorder mediated by the human T cell receptor bearing the TRBV9 family beta-chain, comprising administering to a subject in need of such treatment a pharmaceutical composition according to claim 14 in a therapeutically effective amount.

22. The method for treating a disease or disorder according to claim 21, wherein the disease or disorder is ankylosing spondylitis, celiac disease, T cell leukemia, or T cell lymphoma.

* * * * *